US012458540B2

(12) United States Patent
Bishop et al.

(10) Patent No.: US 12,458,540 B2
(45) Date of Patent: Nov. 4, 2025

(54) NEGATIVE PRESSURE WOUND DRESSING MANAGEMENT SYSTEM

(71) Applicant: CONVATEC TECHNOLOGIES INC., Las Vegas, NV (US)

(72) Inventors: Stephen Bishop, Deeside (GB); Duncan Gilding, Deeside (GB); Bryony Lee, Deeside (GB); Shauna Powell, Deeside (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 724 days.

(21) Appl. No.: 16/989,996

(22) Filed: Aug. 11, 2020

(65) Prior Publication Data

US 2020/0368073 A1 Nov. 26, 2020

Related U.S. Application Data

(63) Continuation of application No. 16/099,999, filed as application No. PCT/US2017/031817 on May 9, 2017, now Pat. No. 10,779,993.

(Continued)

(30) Foreign Application Priority Data

May 9, 2016 (GB) .................................. 1608099.6

(51) Int. Cl.

*A61F 13/05* (2024.01)
*A61F 13/0203* (2024.01)
*A61M 1/00* (2006.01)

(52) U.S. Cl.

CPC ............ *A61F 13/05* (2024.01); *A61F 13/022* (2013.01); *A61M 1/73* (2021.05); *A61M 1/912* (2021.05);

(Continued)

(58) Field of Classification Search

CPC ................ A61F 13/0216; A61F 13/022; A61F 13/00068; A61F 13/0206; A61F 13/00055;

(Continued)

(56) References Cited

U.S. PATENT DOCUMENTS 9,199,012 B2 12/2015 Vitaris et al.
9,662,246 B2 5/2017 Collinson et al.

(Continued)

FOREIGN PATENT DOCUMENTS

CN 102015007 A 4/2011
CN 104884008 A 9/2015

(Continued)

OTHER PUBLICATIONS

Chinese Office Action; State Intellectual Property Office of People's Republic of China; Chinese Patent Application No. 201780042750. 7; Jul. 6, 2021; 6 pages.

(Continued)

*Primary Examiner* — Nicholas J. Weiss
*Assistant Examiner* — Gabriella E Burnette
(74) *Attorney, Agent, or Firm* — TAFT STETTINIUS HOLLISTER LLP; Ryan O. White; Derek B. Lavender

(57) ABSTRACT

A wound exudate management system includes a pump for generating negative pressure, a dressing for covering and protecting a wound of a user, a tube including an interior lumen, the tube disposed between the pump and the dressing such that the pump and the dressing are in fluid communication via the interior lumen. The dressing includes an adhesive layer for adhering the dressing adjacent the wound, a wound contact layer, a pressure dispersion layer, a plurality of layers of absorbent material disposed between the wound contact layer and the pressure dispersion layer, a backing layer having a first surface and a second surface, the first (Continued)

surface of the backing layer being adjacent, and in contact with, the pressure dispersion layer and the adhesive layer, and a flexible connector disposed on the second surface of the backing layer.

20 Claims, 9 Drawing Sheets

Related U.S. Application Data

(60) Provisional application No. 62/370,667, filed on Aug. 3, 2016.

(52) U.S. Cl.
CPC ............ *A61M 1/915* (2021.05); *A61M 1/982* (2021.05); *A61M 1/984* (2021.05); *A61M 1/985* (2021.05); *A61M 2205/18* (2013.01)

(58) Field of Classification Search
CPC .......... A61F 13/00059; A61F 13/0213; A61M 1/0025; A61M 1/0088; A61M 2205/18; A61M 27/00; A61M 1/73; A61M 1/912; A61M 1/915; A61M 1/982; A61M 1/984; A61M 1/985
See application file for complete search history.

(56) References Cited

U.S. PATENT DOCUMENTS

| | | | |
|---|---|---|---|
| 10,016,537 | B2 | 7/2018 | Menon et al. |
| 10,046,096 | B2 | 8/2018 | Askem et al. |
| 10,076,447 | B2 | 9/2018 | Barta et al. |
| 10,076,587 | B2 | 9/2018 | Locke et al. |
| 10,143,784 | B2 | 12/2018 | Walton et al. |
| 10,426,670 | B2 | 10/2019 | von Blucher et al. |
| 10,426,747 | B2 | 10/2019 | Johnson |
| 10,426,874 | B2 | 10/2019 | Chien et al. |
| 10,426,875 | B2 | 10/2019 | Blott et al. |
| 10,426,938 | B2 | 10/2019 | Locke et al. |
| 10,434,015 | B2 | 10/2019 | Taylor et al. |
| 10,434,142 | B2 | 10/2019 | Niazi et al. |
| 10,434,210 | B2 | 10/2019 | Olson et al. |
| 10,434,284 | B2 | 10/2019 | Hanson et al. |
| 10,449,094 | B2 | 10/2019 | Donda et al. |
| D866,756 | S | 11/2019 | Allen et al. |
| 10,463,760 | B2 | 11/2019 | Karthikeyan et al. |
| 10,463,773 | B2 | 11/2019 | Haggstrom et al. |
| 10,470,933 | B2 | 11/2019 | Riesinger |
| 10,470,936 | B2 | 11/2019 | Wohlgemuth et al. |
| 10,471,122 | B2 | 11/2019 | Shi et al. |
| 10,471,190 | B2 | 11/2019 | Locke et al. |
| 10,478,345 | B2 | 11/2019 | Barta et al. |
| 10,478,346 | B2 | 11/2019 | Knutson |
| 10,478,394 | B2 | 11/2019 | Yu |
| 10,485,707 | B2 | 11/2019 | Sexton |
| 10,485,891 | B2 | 11/2019 | Andrews et al. |
| 10,485,892 | B2 | 11/2019 | Hands et al. |
| 10,485,906 | B2 | 11/2019 | Freedman et al. |
| 10,486,135 | B2 | 11/2019 | Yang et al. |
| 10,492,956 | B2 | 12/2019 | Zamierowski |
| 10,493,178 | B2 | 12/2019 | Marchant et al. |
| 10,493,184 | B2 | 12/2019 | Collinson et al. |
| 10,493,185 | B2 | 12/2019 | Stokes et al. |
| 10,500,099 | B2 | 12/2019 | Hung et al. |
| 10,500,103 | B2 | 12/2019 | Croizat et al. |
| 10,500,104 | B2 | 12/2019 | Sookraj |
| 10,500,173 | B2 | 12/2019 | Yang et al. |
| 10,500,235 | B2 | 12/2019 | Wardell |
| 10,500,300 | B2 | 12/2019 | Dybe et al. |
| 10,500,301 | B2 | 12/2019 | Laurensou |
| 10,500,302 | B2 | 12/2019 | Holm et al. |
| 10,501,487 | B2 | 12/2019 | Andrews et al. |
| 10,506,928 | B2 | 12/2019 | Locke et al. |
| 10,507,141 | B2 | 12/2019 | Allen et al. |
| 10,507,259 | B2 | 12/2019 | Cree et al. |
| 10,512,707 | B2 | 12/2019 | Whalen, III et al. |
| 10,525,170 | B2 | 1/2020 | Havenstrite et al. |
| 10,532,137 | B2 | 1/2020 | Pratt et al. |
| 10,532,194 | B2 | 1/2020 | Locke et al. |
| 10,537,657 | B2 | 1/2020 | Phillips et al. |
| 10,542,936 | B2 | 1/2020 | Goldberg et al. |
| 10,543,133 | B2 | 1/2020 | Shaw et al. |
| 10,543,293 | B2 | 1/2020 | Suschek |
| 10,548,777 | B2 | 2/2020 | Locke et al. |
| 10,549,008 | B2 | 2/2020 | Yoo |
| 10,549,016 | B2 | 2/2020 | Bushko et al. |
| 10,549,017 | B2 | 2/2020 | Hsiao et al. |
| 10,555,838 | B2 | 2/2020 | Wu et al. |
| 10,555,839 | B2 | 2/2020 | Hartwell |
| 10,556,044 | B2 | 2/2020 | Robinson et al. |
| 10,561,533 | B2 | 2/2020 | Hoggarth et al. |
| 10,561,536 | B2 | 2/2020 | Holm et al. |
| 10,568,767 | B2 | 2/2020 | Addison et al. |
| 10,568,768 | B2 | 2/2020 | Long et al. |
| 10,568,770 | B2 | 2/2020 | Robinson et al. |
| 10,568,771 | B2 | 2/2020 | MacDonald et al. |
| 10,568,773 | B2 | 2/2020 | Tuck et al. |
| 10,568,983 | B2 | 2/2020 | Gerdes et al. |
| 10,575,991 | B2 | 3/2020 | Dunn |
| 10,575,992 | B2 | 3/2020 | Sarangapani et al. |
| 10,576,037 | B2 | 3/2020 | Harrell |
| 10,576,189 | B2 | 3/2020 | Locke et al. |
| 10,583,042 | B2 | 3/2020 | Sarangapani et al. |
| 10,583,228 | B2 | 3/2020 | Shuler et al. |
| 10,589,007 | B2 | 3/2020 | Coulthard et al. |
| 10,590,184 | B2 | 3/2020 | Kuo |
| 10,610,414 | B2 | 4/2020 | Hartwell et al. |
| 10,610,415 | B2 | 4/2020 | Griffey et al. |
| 10,610,623 | B2 | 4/2020 | Robinson et al. |
| 10,617,569 | B2 | 4/2020 | Bonn |
| 10,617,608 | B2 | 4/2020 | Shin et al. |
| 10,617,769 | B2 | 4/2020 | Huang |
| 10,617,784 | B2 | 4/2020 | Yu et al. |
| 10,617,786 | B2 | 4/2020 | Kluge et al. |
| 10,618,266 | B2 | 4/2020 | Wright et al. |
| 10,624,984 | B2 | 4/2020 | Courage et al. |
| 10,625,002 | B2 | 4/2020 | Locke et al. |
| 10,632,019 | B2 | 4/2020 | Vitaris |
| 10,632,224 | B2 | 4/2020 | Hardy et al. |
| 10,639,206 | B2 | 5/2020 | Hu et al. |
| 10,639,350 | B2 | 5/2020 | Arber et al. |
| 10,639,404 | B2 | 5/2020 | Lichtenstein |
| 10,646,614 | B2 | 5/2020 | Grinstaff et al. |
| 10,653,562 | B2 | 5/2020 | Robinson et al. |
| 10,653,782 | B2 | 5/2020 | Ameer et al. |
| 10,653,810 | B2 | 5/2020 | Datt et al. |
| 10,653,821 | B2 | 5/2020 | Nichols |
| 10,653,823 | B2 | 5/2020 | Bharti et al. |
| 10,660,799 | B2 | 5/2020 | Wu et al. |
| 10,660,851 | B2 | 5/2020 | Millis et al. |
| 10,660,992 | B2 | 5/2020 | Canner et al. |
| 10,660,994 | B2 | 5/2020 | Askem et al. |
| 10,667,955 | B2 | 6/2020 | Allen et al. |
| 10,667,956 | B2 | 6/2020 | Van Holten et al. |
| 10,682,257 | B2 | 6/2020 | Lu |
| 10,682,258 | B2 | 6/2020 | Manwaring et al. |
| 10,682,259 | B2 | 6/2020 | Hunt et al. |
| 10,682,318 | B2 | 6/2020 | Twomey et al. |
| 10,682,386 | B2 | 6/2020 | Ellis-Behnke et al. |
| 10,682,446 | B2 | 6/2020 | Askem et al. |
| 10,687,983 | B2 | 6/2020 | Dahlberg et al. |
| 10,687,985 | B2 | 6/2020 | Lee et al. |
| 10,688,215 | B2 | 6/2020 | Munro et al. |
| 10,688,217 | B2 | 6/2020 | Hanson et al. |
| RE48,117 | E | 7/2020 | Albert et al. |
| 10,702,419 | B2 | 7/2020 | Locke et al. |
| 10,702,420 | B2 | 7/2020 | Hammond et al. |
| 10,703,942 | B2 | 7/2020 | Tunius |
| 10,709,760 | B2 | 7/2020 | Gronberg et al. |
| 10,709,807 | B2 | 7/2020 | Kshirsagar |
| 10,709,883 | B2 | 7/2020 | Spector |
| 10,716,711 | B2 | 7/2020 | Locke et al. |

(56) References Cited

U.S. PATENT DOCUMENTS 10,716,874 B2 7/2020 Koyama et al.
10,729,589 B2 8/2020 Dorian et al.
10,729,590 B2 8/2020 Simmons et al.
10,729,826 B2 8/2020 Lin
10,736,787 B2 8/2020 Hannigan et al.
10,736,788 B2 8/2020 Locke et al.
10,736,985 B2 8/2020 Odermatt et al.
10,737,003 B2 8/2020 Fujisaki
10,743,900 B2 8/2020 Ingram et al.
10,744,040 B2 8/2020 Kazala, Jr. et al.
10,744,041 B2 8/2020 Hartwell
10,744,225 B2 8/2020 Lindgren et al.
10,744,237 B2 8/2020 Guidi et al.
10,744,238 B2 8/2020 Guidi et al.
10,744,239 B2 8/2020 Armstrong et al.
10,744,240 B2 8/2020 Simmons et al.
10,751,212 B2 8/2020 Raza et al.
10,751,442 B2 8/2020 Bonnefin et al.
10,751,452 B2 8/2020 Topaz
10,758,423 B2 9/2020 Pigg et al.
10,758,424 B2 9/2020 Blott et al.
10,758,425 B2 9/2020 Blott et al.
10,758,426 B2 9/2020 Eddy
10,758,651 B2 9/2020 Blott et al.
10,765,561 B2 9/2020 Lattimore et al.
10,765,783 B2 9/2020 Locke et al.
10,772,767 B2 9/2020 Bjork et al.
10,772,999 B2 9/2020 Svensby
10,779,993 B2 9/2020 Bishop et al.
10,780,114 B2 9/2020 Udagawa et al.
10,780,194 B2 9/2020 Flach et al.
10,780,201 B2 9/2020 Lin
10,780,202 B2 9/2020 Askem et al.
10,780,203 B2 9/2020 Coulthard et al.
10,782,238 B2 9/2020 Hicks et al.
10,792,191 B2 10/2020 Robinson et al.
10,792,192 B2 10/2020 Tout et al.
10,792,337 B2 10/2020 Leung et al.
10,792,404 B2 10/2020 Hu et al.
10,792,482 B2 10/2020 Randolph et al.
10,800,905 B2 10/2020 Delli-Santi et al.
10,806,819 B2 10/2020 Shuler
11,058,588 B2 7/2021 Albert et al.
11,147,714 B2 10/2021 Blott et al.
11,154,426 B2 10/2021 Riesinger
11,197,953 B2 12/2021 Heaton et al.
2002/0082567 A1* 6/2002 Lockwood .............. A61F 13/05 604/385.03
2006/0100594 A1 5/2006 Adams et al.
2006/0155260 A1 7/2006 Blott et al.
2006/0172000 A1 8/2006 Cullen et al.
2007/0185426 A1 8/2007 Ambrosio et al.
2007/0219512 A1 9/2007 Heaton et al.
2007/0239078 A1 10/2007 Jaeb
2009/0227969 A1* 9/2009 Jaeb ........................ A61M 1/78 604/313
2009/0234307 A1* 9/2009 Vitaris .................... A61M 1/78 604/304
2009/0259203 A1 10/2009 Hu et al.
2009/0293887 A1 12/2009 Wilkes et al.
2009/0299303 A1 12/2009 Seegert
2010/0015208 A1 1/2010 Kershaw et al.
2010/0030178 A1 2/2010 MacMeccan et al.
2010/0069863 A1* 3/2010 Olson ..................... A61F 13/02 604/385.01
2010/0125233 A1 5/2010 Edward S. et al.
2010/0125258 A1 5/2010 Coulthard et al.
2010/0137775 A1 6/2010 Hu et al.
2010/0185163 A1 7/2010 Heagle
2010/0298790 A1 11/2010 Guidi et al.
2011/0015595 A1 1/2011 Robinson et al.
2011/0028918 A1 2/2011 Hartwell
2011/0106026 A1 5/2011 Wu et al.
2011/0112457 A1 5/2011 Holm et al.
2011/0178451 A1 7/2011 Robinson et al.
2011/0224593 A1 9/2011 Tunius
2011/0224630 A1 9/2011 Simmons et al.
2011/0230849 A1 9/2011 Coulthard et al.
2011/0251566 A1 10/2011 Zimnitsky et al.
2011/0257572 A1 10/2011 Locke et al.
2011/0257573 A1 10/2011 Hong et al.
2011/0275972 A1 11/2011 Rosenberg
2012/0071845 A1 3/2012 Hu et al.
2012/0130332 A1* 5/2012 Cotton ................ A61F 13/0203 112/475.01
2012/0136325 A1 5/2012 Allen et al.
2012/0209226 A1 8/2012 Simmons et al.
2013/0053795 A1 2/2013 Coulthard et al.
2013/0123728 A1 5/2013 Pratt et al.
2013/0211307 A1* 8/2013 Evans ..................... A61F 13/05 602/44
2013/0226063 A1 8/2013 Taylor et al.
2014/0005618 A1 1/2014 Locke et al.
2014/0031771 A1 1/2014 Locke et al.
2014/0074053 A1 3/2014 Locke et al.
2014/0188060 A1 7/2014 Robinson et al.
2014/0194838 A1 7/2014 Wibaux et al.
2014/0200532 A1 7/2014 Robinson et al.
2014/0236112 A1 8/2014 Von Wolff et al.
2014/0256925 A1 9/2014 Catchmark et al.
2014/0276499 A1 9/2014 Locke et al.
2014/0296804 A1 10/2014 Hicks et al.
2014/0308338 A1 10/2014 Nierle et al.
2014/0309574 A1 10/2014 Cotton
2015/0018433 A1 1/2015 Leipzig et al.
2015/0057624 A1 2/2015 Simmons et al.
2015/0071985 A1 3/2015 Walker et al.
2015/0079152 A1 3/2015 Wuollett et al.
2015/0094674 A1 4/2015 Pratt et al.
2015/0104486 A1 4/2015 Bonnefin et al.
2015/0112311 A1 4/2015 Hammond et al.
2015/0119831 A1 4/2015 Robinson et al.
2015/0119834 A1 4/2015 Locke et al.
2015/0141941 A1 5/2015 Allen et al.
2015/0148785 A1 5/2015 Kleiner
2015/0174304 A1 6/2015 Askem et al.
2015/0216733 A1* 8/2015 Allen .................. A61F 13/5376 604/319
2015/0245949 A1 9/2015 Locke et al.
2015/0245950 A1 9/2015 Locke et al.
2015/0246164 A1 9/2015 Heaton et al.
2015/0250979 A1 9/2015 Loske
2015/0265741 A1 9/2015 Duncan et al.
2015/0265743 A1 9/2015 Hanson et al.
2015/0320901 A1 11/2015 Chandrashekhar-Bhat et al.
2015/0351970 A1* 12/2015 Dagger ............. A61F 13/00059 604/361
2016/0008293 A1 1/2016 Shi et al.
2016/0038626 A1 2/2016 Locke et al.
2016/0051724 A1 2/2016 Sahin et al.
2016/0067107 A1 3/2016 Cotton
2016/0100987 A1 4/2016 Hartwell et al.
2016/0106878 A1 4/2016 Yang et al.
2016/0106892 A1 4/2016 Hartwell
2016/0166422 A1 6/2016 Karim et al.
2016/0193244 A1 7/2016 Ota et al.
2016/0222548 A1 8/2016 Agboh
2016/0271178 A1 9/2016 Hauser et al.
2016/0287743 A1 10/2016 Andrews
2016/0339158 A1* 11/2016 Collinson ............. A61M 1/985
2016/0374847 A1 12/2016 Lachenbruch et al.
2017/0014275 A1 1/2017 Schneider
2017/0049111 A1 2/2017 Patton et al.
2017/0072669 A1 3/2017 Sekido et al.
2017/0128269 A1 5/2017 Coulthard et al.
2017/0189236 A1* 7/2017 Locke .................. A61M 1/985
2017/0189237 A1 7/2017 Locke et al.
2017/0189575 A1 7/2017 Lee et al.
2017/0209615 A1 7/2017 Tornero Garcia et al.
2017/0232161 A1 8/2017 Fewkes et al.
2017/0258956 A1 9/2017 Flach et al.
2017/0367895 A1 12/2017 Holm et al.
2017/0368239 A1 12/2017 Askem et al.
2018/0008742 A1 1/2018 Hoggarth et al.

(56) References Cited

U.S. PATENT DOCUMENTS

| | | | |
|---|---|---|---|
| 2018/0014974 | A1 | 1/2018 | Hoggarth et al. |
| 2018/0023217 | A1 | 1/2018 | Patton et al. |
| 2018/0030321 | A1 | 2/2018 | Tunius |
| 2018/0042789 | A1 | 2/2018 | Bradford et al. |
| 2018/0078423 | A1 | 3/2018 | Magin et al. |
| 2018/0086903 | A1 | 3/2018 | Zhang et al. |
| 2018/0118809 | A1 | 5/2018 | Mearns Spragg |
| 2018/0133066 | A1 | 5/2018 | Ahsani et al. |
| 2018/0140467 | A1 | 5/2018 | Hunt |
| 2018/0140822 | A1 | 5/2018 | Robinson et al. |
| 2018/0200414 | A1 | 7/2018 | Askem et al. |
| 2018/0221531 | A1 | 8/2018 | Bender et al. |
| 2018/0236124 | A1 | 8/2018 | Young et al. |
| 2018/0243463 | A1 | 8/2018 | Chatterjee et al. |
| 2018/0243464 | A1 | 8/2018 | Hwang et al. |
| 2018/0244857 | A1 | 8/2018 | Lee et al. |
| 2018/0272052 | A1 | 9/2018 | Locke et al. |
| 2018/0296397 | A1 | 10/2018 | Askem et al. |
| 2018/0303873 | A1 | 10/2018 | Been et al. |
| 2018/0311419 | A1 | 11/2018 | Locke et al. |
| 2018/0333522 | A1 | 11/2018 | Pratt et al. |
| 2018/0344533 | A1 | 12/2018 | Rovaniemi |
| 2018/0353334 | A1 | 12/2018 | Locke et al. |
| 2018/0353337 | A1 | 12/2018 | Locke |
| 2018/0353339 | A1 | 12/2018 | Locke et al. |
| 2018/0353340 | A1 | 12/2018 | Robinson et al. |
| 2018/0353344 | A1 | 12/2018 | Locke et al. |
| 2018/0353662 | A1 | 12/2018 | Locke et al. |
| 2018/0353663 | A1 | 12/2018 | Locke et al. |
| 2018/0360667 | A1 | 12/2018 | Droche |
| 2019/0000677 | A1 | 1/2019 | Munro |
| 2019/0015258 | A1 | 1/2019 | Gowans et al. |
| 2019/0015468 | A1 | 1/2019 | Yadav et al. |
| 2019/0030223 | A1 | 1/2019 | Lin |
| 2019/0046682 | A1 | 2/2019 | Choi et al. |
| 2019/0060127 | A1 | 2/2019 | Locke et al. |
| 2019/0083752 | A1 | 3/2019 | Howell et al. |
| 2019/0117465 | A1 | 4/2019 | Osborne et al. |
| 2019/0117466 | A1 | 4/2019 | Kazala, Jr. et al. |
| 2019/0117861 | A1 | 4/2019 | Locke et al. |
| 2019/0125590 | A1 | 5/2019 | Rehbein et al. |
| 2019/0133830 | A1 | 5/2019 | Bishop et al. |
| 2019/0151155 | A1 | 5/2019 | Bonn |
| 2019/0151159 | A1 | 5/2019 | Gowans et al. |
| 2019/0151495 | A1 | 5/2019 | Helary et al. |
| 2019/0184052 | A1 | 6/2019 | Ilan et al. |
| 2019/0231600 | A1 | 8/2019 | Locke et al. |
| 2019/0231602 | A1 | 8/2019 | Locke et al. |
| 2019/0231943 | A1 | 8/2019 | Robinson et al. |
| 2019/0274889 | A1 | 9/2019 | Steward et al. |
| 2019/0282728 | A1 | 9/2019 | Kellar et al. |
| 2019/0290799 | A1 | 9/2019 | Arshi et al. |
| 2019/0298249 | A1 | 10/2019 | Bates et al. |
| 2019/0298577 | A1 | 10/2019 | Locke et al. |
| 2019/0298578 | A1 | 10/2019 | Shulman et al. |
| 2019/0298579 | A1 | 10/2019 | Moore et al. |
| 2019/0298580 | A1 | 10/2019 | Hall et al. |
| 2019/0298582 | A1 | 10/2019 | Addison et al. |
| 2019/0298881 | A1 | 10/2019 | Ramjit et al. |
| 2019/0298882 | A1 | 10/2019 | Nelson |
| 2019/0298895 | A1 | 10/2019 | Selby et al. |
| 2019/0307611 | A1 | 10/2019 | Askem et al. |
| 2019/0307612 | A1 | 10/2019 | Hartwell et al. |
| 2019/0307934 | A1 | 10/2019 | Allen et al. |
| 2019/0307935 | A1 | 10/2019 | Simmons et al. |
| 2019/0314187 | A1 | 10/2019 | Emslander et al. |
| 2019/0314209 | A1 | 10/2019 | Ha et al. |
| 2019/0314544 | A1 | 10/2019 | Filho et al. |
| 2019/0321232 | A1 | 10/2019 | Jardret et al. |
| 2019/0321509 | A1 | 10/2019 | Chakravarthy et al. |
| 2019/0321526 | A1 | 10/2019 | Robinson et al. |
| 2019/0322795 | A1 | 10/2019 | Kubo et al. |
| 2019/0328580 | A1 | 10/2019 | Emslander et al. |
| 2019/0336343 | A1 | 11/2019 | Etchells et al. |
| 2019/0336344 | A1 | 11/2019 | Locke |
| 2019/0336345 | A1 | 11/2019 | Bannwart |
| 2019/0336346 | A1 | 11/2019 | Locke et al. |
| 2019/0336640 | A1 | 11/2019 | Vismara et al. |
| 2019/0336641 | A1 | 11/2019 | Nisbet |
| 2019/0336643 | A1 | 11/2019 | Luukko et al. |
| 2019/0336658 | A1 | 11/2019 | Heaton et al. |
| 2019/0336739 | A1 | 11/2019 | Locke et al. |
| 2019/0343687 | A1 | 11/2019 | Locke et al. |
| 2019/0343889 | A1 | 11/2019 | Luukko et al. |
| 2019/0343979 | A1 | 11/2019 | Kearney et al. |
| 2019/0343993 | A1 | 11/2019 | Weston |
| 2019/0343994 | A1 | 11/2019 | Greener |
| 2019/0344242 | A1 | 11/2019 | Kim et al. |
| 2019/0350763 | A1 | 11/2019 | Pratt et al. |
| 2019/0350764 | A1 | 11/2019 | Zochowski et al. |
| 2019/0350765 | A1 | 11/2019 | Heagle et al. |
| 2019/0350775 | A1 | 11/2019 | Biasutti et al. |
| 2019/0350970 | A1 | 11/2019 | Saphier et al. |
| 2019/0351092 | A1 | 11/2019 | Silver et al. |
| 2019/0351093 | A1 | 11/2019 | Stein et al. |
| 2019/0351094 | A1 | 11/2019 | Maher et al. |
| 2019/0351095 | A1 | 11/2019 | Maher et al. |
| 2019/0351111 | A1 | 11/2019 | Locke et al. |
| 2019/0358088 | A1 | 11/2019 | Lavocah et al. |
| 2019/0358089 | A1 | 11/2019 | Dagger et al. |
| 2019/0358361 | A1 | 11/2019 | McInnes et al. |
| 2019/0358372 | A1 | 11/2019 | Askem et al. |
| 2019/0365948 | A1 | 12/2019 | Deegan et al. |
| 2019/0365962 | A1 | 12/2019 | Lee et al. |
| 2019/0374408 | A1 | 12/2019 | Robles et al. |
| 2019/0374673 | A1 | 12/2019 | Hoefinghoff et al. |
| 2019/0380878 | A1 | 12/2019 | Edwards et al. |
| 2019/0380881 | A1 | 12/2019 | Albert et al. |
| 2019/0380882 | A1 | 12/2019 | Taylor et al. |
| 2019/0380883 | A1 | 12/2019 | Macphee et al. |
| 2019/0381222 | A9 | 12/2019 | Locke et al. |
| 2019/0388577 | A1 | 12/2019 | Chandrashekhar-Bhat et al. |
| 2019/0388579 | A1 | 12/2019 | Macphee et al. |
| 2019/0388589 | A1 | 12/2019 | Macphee et al. |
| 2020/0000640 | A1 | 1/2020 | Mondal et al. |
| 2020/0000642 | A1 | 1/2020 | Waite |
| 2020/0000643 | A1 | 1/2020 | Locke |
| 2020/0000955 | A1 | 1/2020 | Andrews et al. |
| 2020/0000956 | A1 | 1/2020 | Huang et al. |
| 2020/0000960 | A1 | 1/2020 | Kellar et al. |
| 2020/0000985 | A1 | 1/2020 | Seddon et al. |
| 2020/0008981 | A1 | 1/2020 | Wheldrake |
| 2020/0009289 | A1 | 1/2020 | Torabinejad et al. |
| 2020/0009400 | A1 | 1/2020 | Ribeiro et al. |
| 2020/0017650 | A1 | 1/2020 | Young et al. |
| 2020/0022844 | A1 | 1/2020 | Blott et al. |
| 2020/0023102 | A1 | 1/2020 | Powell |
| 2020/0023103 | A1 | 1/2020 | Joshi et al. |
| 2020/0023104 | A1 | 1/2020 | Eriksson et al. |
| 2020/0023105 | A1 | 1/2020 | Long et al. |
| 2020/0023106 | A1 | 1/2020 | Carroll et al. |
| 2020/0030153 | A1 | 1/2020 | Johannison et al. |
| 2020/0030480 | A1 | 1/2020 | Choi |
| 2020/0030499 | A1 | 1/2020 | Menon et al. |
| 2020/0038023 | A1 | 2/2020 | Dunn |
| 2020/0038249 | A1 | 2/2020 | Pratt et al. |
| 2020/0038250 | A1 | 2/2020 | Edwards et al. |
| 2020/0038251 | A1 | 2/2020 | Locke et al. |
| 2020/0038252 | A1 | 2/2020 | Spiro |
| 2020/0038283 | A1 | 2/2020 | Hall et al. |
| 2020/0038470 | A1 | 2/2020 | Datt et al. |
| 2020/0038544 | A1 | 2/2020 | Grover et al. |
| 2020/0038546 | A1 | 2/2020 | Dizio et al. |
| 2020/0038639 | A1 | 2/2020 | Patel et al. |
| 2020/0046565 | A1 | 2/2020 | Barta et al. |
| 2020/0046566 | A1 | 2/2020 | Carey et al. |
| 2020/0046567 | A1 | 2/2020 | Carroll et al. |
| 2020/0046568 | A1 | 2/2020 | Sexton |
| 2020/0046663 | A1 | 2/2020 | Murdock et al. |
| 2020/0046876 | A1 | 2/2020 | Liu |
| 2020/0046887 | A1 | 2/2020 | Runquist et al. |
| 2020/0054491 | A1 | 2/2020 | Hentrich et al. |
| 2020/0054781 | A1 | 2/2020 | Weiser et al. |
| 2020/0060879 | A1 | 2/2020 | Edwards et al. |

(56) References Cited

U.S. PATENT DOCUMENTS

| | | | |
|---|---|---|---|
| 2020/0061253 | A1 | 2/2020 | Long et al. |
| 2020/0061254 | A1 | 2/2020 | Joshi et al. |
| 2020/0061379 | A1 | 2/2020 | Bogie et al. |
| 2020/0069183 | A1 | 3/2020 | Rice et al. |
| 2020/0069476 | A1 | 3/2020 | Randolph et al. |
| 2020/0069477 | A1 | 3/2020 | Holm et al. |
| 2020/0069478 | A1 | 3/2020 | Jabbarzadeh et al. |
| 2020/0069479 | A1 | 3/2020 | Buan et al. |
| 2020/0069835 | A1 | 3/2020 | Hissink et al. |
| 2020/0069850 | A1 | 3/2020 | Beadle et al. |
| 2020/0069851 | A1 | 3/2020 | Blott et al. |
| 2020/0069853 | A1 | 3/2020 | Hall et al. |
| 2020/0078223 | A1 | 3/2020 | Locke et al. |
| 2020/0078224 | A1 | 3/2020 | Carroll et al. |
| 2020/0078225 | A1 | 3/2020 | Grillitsch et al. |
| 2020/0078305 | A1 | 3/2020 | Auvinen et al. |
| 2020/0078330 | A1 | 3/2020 | Gay |
| 2020/0078482 | A1 | 3/2020 | Yoon et al. |
| 2020/0078499 | A1 | 3/2020 | Gadde et al. |
| 2020/0085625 | A1 | 3/2020 | Bellini et al. |
| 2020/0085626 | A1 | 3/2020 | Braga et al. |
| 2020/0085629 | A1 | 3/2020 | Locke et al. |
| 2020/0085630 | A1 | 3/2020 | Robinson et al. |
| 2020/0085632 | A1 | 3/2020 | Locke et al. |
| 2020/0085991 | A1 | 3/2020 | Coomber |
| 2020/0085992 | A1 | 3/2020 | Locke et al. |
| 2020/0086014 | A1 | 3/2020 | Locke et al. |
| 2020/0086017 | A1 | 3/2020 | Jardret et al. |
| 2020/0086049 | A1 | 3/2020 | Park et al. |
| 2020/0093646 | A1 | 3/2020 | Locke et al. |
| 2020/0093756 | A1 | 3/2020 | Sabacinski |
| 2020/0093953 | A1 | 3/2020 | Kim et al. |
| 2020/0093954 | A1 | 3/2020 | Leise, III |
| 2020/0093970 | A1 | 3/2020 | Hunt et al. |
| 2020/0095421 | A1 | 3/2020 | Kettel |
| 2020/0100945 | A1 | 4/2020 | Albert et al. |
| 2020/0101192 | A1 | 4/2020 | Folwarzny |
| 2020/0107964 | A1 | 4/2020 | Locke et al. |
| 2020/0107965 | A1 | 4/2020 | Greener |
| 2020/0107966 | A1 | 4/2020 | Francis |
| 2020/0107967 | A1 | 4/2020 | Holm et al. |
| 2020/0108169 | A1 | 4/2020 | Hu et al. |
| 2020/0113741 | A1 | 4/2020 | Rehbein et al. |
| 2020/0114039 | A1 | 4/2020 | Wang et al. |
| 2020/0114040 | A1 | 4/2020 | Waite et al. |
| 2020/0114049 | A1 | 4/2020 | Wall |
| 2020/0121509 | A1 | 4/2020 | Locke et al. |
| 2020/0121510 | A1 | 4/2020 | Hartwell et al. |
| 2020/0121513 | A1 | 4/2020 | Townsend et al. |
| 2020/0121521 | A1 | 4/2020 | Daniel et al. |
| 2020/0121833 | A9 | 4/2020 | Askem et al. |
| 2020/0129338 | A1 | 4/2020 | Gardiner et al. |
| 2020/0129341 | A1 | 4/2020 | Coulthard et al. |
| 2020/0129648 | A1 | 4/2020 | Drury et al. |
| 2020/0129654 | A1 | 4/2020 | Bouvier et al. |
| 2020/0129655 | A1 | 4/2020 | Gardiner et al. |
| 2020/0129675 | A1 | 4/2020 | Robinson et al. |
| 2020/0138754 | A1 | 5/2020 | Johnson |
| 2020/0139002 | A1 | 5/2020 | Dudnyk et al. |
| 2020/0139023 | A1 | 5/2020 | Haggstrom et al. |
| 2020/0139025 | A1 | 5/2020 | Robinson et al. |
| 2020/0141031 | A1 | 5/2020 | Kosan et al. |
| 2020/0146894 | A1 | 5/2020 | Long et al. |
| 2020/0146896 | A1 | 5/2020 | Rice et al. |
| 2020/0146897 | A1 | 5/2020 | Locke et al. |
| 2020/0146899 | A1 | 5/2020 | Pratt et al. |
| 2020/0155355 | A1 | 5/2020 | Hill et al. |
| 2020/0155358 | A1 | 5/2020 | Wheldrake |
| 2020/0155359 | A1 | 5/2020 | Carroll et al. |
| 2020/0155361 | A1 | 5/2020 | Pigg et al. |
| 2020/0155379 | A1 | 5/2020 | Shaw et al. |
| 2020/0163802 | A1 | 5/2020 | Hunt et al. |
| 2020/0163803 | A1 | 5/2020 | Pigg et al. |
| 2020/0164112 | A1 | 5/2020 | Kato et al. |
| 2020/0164120 | A1 | 5/2020 | Jaecklein et al. |
| 2020/0170841 | A1 | 6/2020 | Waite et al. |
| 2020/0170842 | A1 | 6/2020 | Locke |
| 2020/0170843 | A1 | 6/2020 | Collinson et al. |
| 2020/0171197 | A1 | 6/2020 | Hubbell et al. |
| 2020/0179300 | A1 | 6/2020 | Urban et al. |
| 2020/0179558 | A1 | 6/2020 | Munro et al. |
| 2020/0179673 | A1 | 6/2020 | Wan |
| 2020/0188179 | A1 | 6/2020 | Bugedo-Albizuri et al. |
| 2020/0188180 | A1 | 6/2020 | Akbari et al. |
| 2020/0188182 | A1 | 6/2020 | Sanders et al. |
| 2020/0188183 | A1 | 6/2020 | Hamerslagh et al. |
| 2020/0188550 | A1 | 6/2020 | Dagger et al. |
| 2020/0188564 | A1 | 6/2020 | Dunn |
| 2020/0190310 | A1 | 6/2020 | Meyer |
| 2020/0197227 | A1 | 6/2020 | Locke et al. |
| 2020/0197228 | A1 | 6/2020 | Hartwell |
| 2020/0197559 | A1 | 6/2020 | Bourdillon et al. |
| 2020/0197580 | A1 | 6/2020 | Kilpadi et al. |
| 2020/0206035 | A1 | 7/2020 | Kantor et al. |
| 2020/0206036 | A1 | 7/2020 | Robinson et al. |
| 2020/0214637 | A1 | 7/2020 | Brownhill et al. |
| 2020/0214897 | A1 | 7/2020 | Long et al. |
| 2020/0214898 | A1 | 7/2020 | Waite et al. |
| 2020/0214899 | A1 | 7/2020 | Locke et al. |
| 2020/0215220 | A1 | 7/2020 | Schomburg et al. |
| 2020/0215226 | A1 | 7/2020 | Kitagawa et al. |
| 2020/0222469 | A1 | 7/2020 | Cotton |
| 2020/0229983 | A1 | 7/2020 | Robinson et al. |
| 2020/0230283 | A1 | 7/2020 | Yang et al. |
| 2020/0237562 | A1 | 7/2020 | Rice et al. |
| 2020/0237564 | A1 | 7/2020 | Hammond et al. |
| 2020/0237816 | A1 | 7/2020 | Lait |
| 2020/0246190 | A1 | 8/2020 | Luckemeyer et al. |
| 2020/0246191 | A1 | 8/2020 | Lu et al. |
| 2020/0246194 | A1 | 8/2020 | Gonzalez et al. |
| 2020/0246195 | A1 | 8/2020 | Robinson et al. |
| 2020/0253785 | A1 | 8/2020 | Bernet et al. |
| 2020/0253786 | A1 | 8/2020 | Harrison et al. |
| 2020/0253788 | A1 | 8/2020 | Rehbein et al. |
| 2020/0254139 | A1 | 8/2020 | Phillips et al. |
| 2020/0261275 | A1 | 8/2020 | Manwaring et al. |
| 2020/0261276 | A1 | 8/2020 | Lujan Hernandez et al. |
| 2020/0268560 | A1 | 8/2020 | Harrison et al. |
| 2020/0268561 | A1 | 8/2020 | Locke et al. |
| 2020/0269028 | A1 | 8/2020 | Hegg |
| 2020/0270484 | A1 | 8/2020 | Lipscomb et al. |
| 2020/0276055 | A1 | 9/2020 | Randolph et al. |
| 2020/0276058 | A1 | 9/2020 | Locke et al. |
| 2020/0277450 | A1 | 9/2020 | Silverstein et al. |
| 2020/0281519 | A1 | 9/2020 | Gowans et al. |
| 2020/0281529 | A1 | 9/2020 | Grubb et al. |
| 2020/0281678 | A1 | 9/2020 | Long et al. |
| 2020/0281775 | A1 | 9/2020 | Kushnir et al. |
| 2020/0282100 | A1 | 9/2020 | Gil et al. |
| 2020/0282114 | A1 | 9/2020 | Long et al. |
| 2020/0282115 | A1 | 9/2020 | Gardner et al. |
| 2020/0289326 | A1 | 9/2020 | Nielsen et al. |
| 2020/0289327 | A1 | 9/2020 | Hansen et al. |
| 2020/0289328 | A1 | 9/2020 | Luckemeyer et al. |
| 2020/0289346 | A1 | 9/2020 | Hansen et al. |
| 2020/0289347 | A1 | 9/2020 | Gowans et al. |
| 2020/0289701 | A1 | 9/2020 | Hall et al. |
| 2020/0289712 | A1 | 9/2020 | Jiang et al. |
| 2020/0289723 | A1 | 9/2020 | Gregory et al. |
| 2020/0289726 | A1 | 9/2020 | Locke et al. |
| 2020/0289727 | A1 | 9/2020 | Locke |
| 2020/0289806 | A1 | 9/2020 | Locke et al. |
| 2020/0297541 | A1 | 9/2020 | Hartwell et al. |
| 2020/0297543 | A1 | 9/2020 | Rodzewicz et al. |
| 2020/0297544 | A1 | 9/2020 | Moine et al. |
| 2020/0297892 | A1 | 9/2020 | Silcock |
| 2020/0297893 | A1 | 9/2020 | Ericson |
| 2020/0297894 | A1 | 9/2020 | Koyama et al. |
| 2020/0299865 | A1 | 9/2020 | Bonnefin et al. |
| 2020/0306089 | A1 | 10/2020 | Delury et al. |
| 2020/0306091 | A1 | 10/2020 | Lee et al. |
| 2020/0306092 | A1 | 10/2020 | Rehbein et al. |
| 2020/0306094 | A1 | 10/2020 | Kushnir et al. |
| 2020/0306426 | A1 | 10/2020 | Rice et al. |

(56) References Cited

U.S. PATENT DOCUMENTS

| | | | |
|---|---|---|---|
| 2020/0306428 | A1 | 10/2020 | Ingram et al. |
| 2020/0306430 | A1 | 10/2020 | Rehbein et al. |
| 2020/0315853 | A1 | 10/2020 | Waite |
| 2020/0315854 | A1 | 10/2020 | Simmons et al. |
| 2020/0315894 | A1 | 10/2020 | Churilla et al. |
| 2020/0316271 | A1 | 10/2020 | Lin |
| 2020/0316272 | A1 | 10/2020 | Simpson |
| 2020/0316273 | A1 | 10/2020 | Hegg |
| 2020/0323692 | A1 | 10/2020 | Locke et al. |
| 2020/0324015 | A1 | 10/2020 | Kettel et al. |
| 2020/0330283 | A1 | 10/2020 | Locke et al. |
| 2020/0330284 | A1 | 10/2020 | Locke et al. |
| 2020/0330285 | A1 | 10/2020 | Rehbein et al. |
| 2020/0330658 | A1 | 10/2020 | Fujisaki |
| 2020/0330660 | A1 | 10/2020 | Patel et al. |
| 2020/0337719 | A1 | 10/2020 | Ingram et al. |
| 2020/0337904 | A1 | 10/2020 | Waite |
| 2020/0337905 | A1 | 10/2020 | Earl et al. |
| 2020/0337906 | A1 | 10/2020 | Long et al. |
| 2020/0337908 | A1 | 10/2020 | Long et al. |
| 2020/0338228 | A1 | 10/2020 | Kharkar et al. |
| 2020/0338243 | A1 | 10/2020 | Harrison et al. |
| 2021/0228417 | A1 | 7/2021 | Ha et al. |
| 2021/0244571 | A1 | 8/2021 | Dunn |
| 2022/0023527 | A1 | 1/2022 | Beadle et al. |
| 2022/0062060 | A1 | 3/2022 | Hu et al. |
| 2022/0062526 | A1 | 3/2022 | Heaton et al. |
| 2022/0117794 | A1 | 4/2022 | Hartwell et al. |

FOREIGN PATENT DOCUMENTS

| | | | | |
|---|---|---|---|---|
| CN | 104884010 | A | 9/2015 | |
| EP | 1022009 | A2 * | 7/2000 | ............ A61F 13/51 |
| EP | 2103290 | A2 | 9/2009 | |
| EP | 3187204 | A1 | 7/2017 | |
| EP | 3556407 | A1 | 10/2019 | |
| EP | 3569260 | A1 | 11/2019 | |
| EP | 3622975 | A1 | 3/2020 | |
| EP | 3643328 | A1 | 4/2020 | |
| EP | 3643330 | A1 | 4/2020 | |
| EP | 3643331 | A1 | 4/2020 | |
| EP | 3669838 | A1 | 6/2020 | |
| EP | 3669843 | A1 | 6/2020 | |
| EP | 3669844 | A1 | 6/2020 | |
| EP | 3669898 | A1 | 6/2020 | |
| EP | 3669899 | A1 | 6/2020 | |
| EP | 3827795 | A1 | 6/2021 | |
| EP | 3060181 | B1 | 11/2021 | |
| EP | 3104816 | B1 | 12/2021 | |
| EP | 3939554 | A1 | 1/2022 | |
| EP | 3454807 | B1 | 4/2022 | |
| EP | 3586805 | B1 | 4/2022 | |
| EP | 3871645 | B1 | 5/2022 | |
| EP | 3315145 | B1 | 6/2022 | |
| GB | 2380945 | A | 4/2003 | |
| GB | 2560365 | B | 9/2018 | |
| GB | 2579211 | A | 6/2020 | |
| GB | 2579368 | A | 6/2020 | |
| JP | 2002534214 | A | 10/2002 | |
| JP | 2008544794 | A | 12/2008 | |
| JP | 2009219869 | A | 10/2009 | |
| JP | 2012502745 | A | 2/2012 | |
| JP | 2014511110 | A | 5/2014 | |
| JP | 2016508061 | A | 3/2016 | |
| KR | 1020110056415 | A | 5/2011 | |
| WO | 2005018543 | A2 | 3/2005 | |
| WO | 2007003905 | A1 | 1/2007 | |
| WO | 2009145703 | A1 | 12/2009 | |
| WO | 2010033574 | A1 | 3/2010 | |
| WO | 2011121394 | A1 | 10/2011 | |
| WO | 2011130570 | A1 | 10/2011 | |
| WO | 2011135284 | A1 | 11/2011 | |
| WO | 2011144888 | A1 | 11/2011 | |
| WO | 2013015827 | A2 | 1/2013 | |
| WO | 2013126049 | A1 | 8/2013 | |
| WO | 2013175306 | A2 | 11/2013 | |
| WO | 2014014842 | A1 | 1/2014 | |
| WO | 2015052219 | A1 | 4/2015 | |
| WO | 2015065612 | A1 | 5/2015 | |
| WO | 2015145117 | A1 | 10/2015 | |
| WO | 2015173546 | A1 | 11/2015 | |
| WO | 2016141450 | A1 | 9/2016 | |
| WO | 2017016974 | A1 | 2/2017 | |
| WO | 2017087163 | A1 | 5/2017 | |
| WO | 2017125250 | A1 | 7/2017 | |
| WO | 2018029231 | A1 | 2/2018 | |
| WO | 2018094061 | A1 | 5/2018 | |
| WO | 2018162613 | A1 | 9/2018 | |
| WO | 2018163093 | A1 | 9/2018 | |
| WO | 2018189265 | A1 | 10/2018 | |
| WO | 2018226667 | A1 | 12/2018 | |
| WO | 2018227144 | A1 | 12/2018 | |
| WO | 2018231825 | A1 | 12/2018 | |
| WO | 2018236648 | A1 | 12/2018 | |
| WO | 2019002085 | A1 | 1/2019 | |
| WO | 2019012068 | A1 | 1/2019 | |
| WO | 2019012069 | A1 | 1/2019 | |
| WO | 2019022493 | A1 | 1/2019 | |
| WO | 2019027933 | A1 | 2/2019 | |
| WO | 2019038548 | A1 | 2/2019 | |
| WO | 2019038549 | A1 | 2/2019 | |
| WO | 2019040656 | A1 | 2/2019 | |
| WO | 2019050855 | A1 | 3/2019 | |
| WO | 2019058373 | A1 | 3/2019 | |
| WO | 2019073326 | A1 | 4/2019 | |
| WO | 2019083563 | A1 | 5/2019 | |
| WO | 2019083868 | A1 | 5/2019 | |
| WO | 2019086911 | A1 | 5/2019 | |
| WO | 2019091150 | A1 | 5/2019 | |
| WO | 2019094147 | A1 | 5/2019 | |
| WO | 2019096828 | A1 | 5/2019 | |
| WO | 2019113275 | A1 | 6/2019 | |
| WO | 2019113623 | A1 | 6/2019 | |
| WO | 2019191590 | A1 | 10/2019 | |
| WO | 2019193141 | A1 | 10/2019 | |
| WO | 2019193333 | A1 | 10/2019 | |
| WO | 2019199389 | A1 | 10/2019 | |
| WO | 2019199596 | A1 | 10/2019 | |
| WO | 2019199687 | A1 | 10/2019 | |
| WO | 2019199798 | A1 | 10/2019 | |
| WO | 2019199849 | A1 | 10/2019 | |
| WO | 2019200035 | A1 | 10/2019 | |
| WO | 2019215572 | A1 | 11/2019 | |
| WO | 2019219613 | A1 | 11/2019 | |
| WO | 2019234365 | A1 | 12/2019 | |
| WO | 2020005062 | A1 | 1/2020 | |
| WO | 2020005344 | A1 | 1/2020 | |
| WO | 2020005536 | A1 | 1/2020 | |
| WO | 2020005546 | A1 | 1/2020 | |
| WO | 2020005577 | A1 | 1/2020 | |
| WO | 2020007429 | A1 | 1/2020 | |
| WO | 2020011691 | A1 | 1/2020 | |
| WO | 2020014178 | A1 | 1/2020 | |
| WO | 2020014310 | A1 | 1/2020 | |
| WO | 2020018300 | A1 | 1/2020 | |
| WO | 2020026061 | A1 | 2/2020 | |
| WO | 2020026144 | A1 | 2/2020 | |
| WO | 2020033351 | A1 | 2/2020 | |
| WO | 2020035811 | A1 | 2/2020 | |
| WO | 2020043665 | A1 | 3/2020 | |
| WO | 2020044237 | A1 | 3/2020 | |
| WO | 2020046443 | A1 | 3/2020 | |
| WO | 2020047255 | A1 | 3/2020 | |
| WO | 2020049038 | A1 | 3/2020 | |
| WO | 2020055945 | A1 | 3/2020 | |
| WO | 2020056014 | A1 | 3/2020 | |
| WO | 2020056182 | A1 | 3/2020 | |
| WO | 2020065531 | A1 | 4/2020 | |
| WO | 2020070231 | A1 | 4/2020 | |
| WO | 2020074512 | A1 | 4/2020 | |
| WO | 2020078993 | A1 | 4/2020 | |
| WO | 2020079009 | A1 | 4/2020 | |
| WO | 2020079330 | A1 | 4/2020 | |
| WO | 2020081259 | A1 | 4/2020 | |

(56) References Cited

FOREIGN PATENT DOCUMENTS

| | | | |
|---|---|---|---|
| WO | 2020081391 | A1 | 4/2020 |
| WO | 2020092598 | A1 | 5/2020 |
| WO | 2020136555 | A1 | 7/2020 |
| WO | 2020141059 | A1 | 7/2020 |
| WO | 2020144347 | A1 | 7/2020 |
| WO | 2020150548 | A1 | 7/2020 |
| WO | 2020159675 | A1 | 8/2020 |
| WO | 2020159677 | A1 | 8/2020 |
| WO | 2020159678 | A1 | 8/2020 |
| WO | 2020159823 | A1 | 8/2020 |
| WO | 2020159859 | A1 | 8/2020 |
| WO | 2020159892 | A1 | 8/2020 |
| WO | 2020161086 | A1 | 8/2020 |
| WO | 2020173665 | A1 | 9/2020 |
| WO | 2020173760 | A1 | 9/2020 |
| WO | 2020174264 | A1 | 9/2020 |
| WO | 2020174510 | A1 | 9/2020 |
| WO | 2020182887 | A1 | 9/2020 |
| WO | 2020185810 | A1 | 9/2020 |
| WO | 2020197759 | A1 | 10/2020 |
| WO | 2020197760 | A1 | 10/2020 |
| WO | 2020198484 | A1 | 10/2020 |
| WO | 2020201879 | A1 | 10/2020 |
| WO | 2020213998 | A1 | 10/2020 |

OTHER PUBLICATIONS

Communication Pursuant to Article 94(3) EPC; European Patent Office; European Application No. 17796717.1; Sep. 10, 2020; 6 pages.

Office Action Summary; Japanese Patent Application No. 2021-153236; Jun. 21, 2022; 4 pages.

Chinese Patent Office; First Office Action with machine-generated English translation of text; Dated: Aug. 31, 2024; Corresponding Chinese Patent Application No. 202210593363.5; pp. 6.

* cited by examiner

NEGATIVE PRESSURE WOUND DRESSING MANAGEMENT SYSTEM

CROSS-REFERENCE TO RELATED APPLICATIONS

This is a continuation application, which claims the benefit of U.S. application Ser. No. 16/099,999, filed on Nov. 8, 2018, which is a U.S. National Phase of International Application No. PCT/US2017/031817, filed on May 9, 2017, which claims the benefit of U.K. Patent Application No. 1608099.6, filed May 9, 2016, and U.S. Provisional Patent Application No. 62/370,667, filed Aug. 3, 2016, all of which are expressly incorporated herein by reference in their entirety and made a part hereof.

TECHNICAL FIELD

The present disclosure generally relates to wound dressing systems, and in particular, to a wound dressing system for use with a negative-pressure pump. Further, the present invention relates to dressings, systems and kits for treating a wound with a dressing that can be used with a source of negative pressure to deliver negative pressure therapy. The dressing is suitable for the treatment of a variety of wounds including chronic and acute types including infected wounds, venous ulcers, diabetic ulcers, burns, surgical wounds and the like.

BACKGROUND

Wound dressings are known and are generally suitable for treating a variety of wounds, including chronic and acute wound types, such as infected wounds, venous ulcers, diabetic ulcers, burns and surgical wounds.

Negative pressure has been used to treat a range of chronic and acute wounds. Negative pressure may facilitate wound healing through a number of mechanisms, including removal of excess exudate, reduction in periwound edema and increased perfusion. Combined with the physical forces exerted by the negative pressure which draw the wound edges together, this can result in improved wound outcomes. Conventional devices are generally large and require the use of sophisticated equipment which may include a suction pump to generate negative pressure, a pressure regulator, canisters for the collection of wound exudate and a wound dressing to deliver the therapy to the wound site. As a result, such devices may be bulky, costly and confine the patient to bed or at least render the patient immobile and unable to go about their usual activities.

More recently, portable systems have been developed which include a means to manage the exudate produced by the wound by collecting exudate within the wound dressing, typically in an absorbent material, and by evaporation through the dressing. Such systems mean that a separate collection canister may not be an essential part of the system. Such a system is described in EP 2021046. An advantage of not needing a canister is that the device is less bulky and more portable. A disadvantage with such devices is that if the dressing exceeds its fluid handling capacity, exudate may be drawn from the absorbent material(s) and enter the pump.

The presence of exudate in the pump will eventually cause it to fail and require its replacement. The therapy provided by the system may also be less than optimal due to the potential for excess exudate to collect at the wound interface. In order to prevent fouling of the pump with exudate, it is known to provide a barrier layer between the absorbent material and the pump. The liquid barrier layer does not however give the user of the device or care giver an indication that the dressing has exceeded its fluid handling capacity and needs to be changed.

In those devices where a canister is present, the user or care giver is given a visual indication of how much exudate is being produced by the wound by the presence of exudate in the canister. The presence of exudate in the canister will however only occur once the dressing has exceeded its fluid handling capacity. There is no early warning that the dressing needs to be changed.

There exists a need for an indication that the dressing has reached or exceeded its fluid handling capacity.

Additionally, existing portable negative-pressure wound dressing systems often include rigid dressing and connection components, adversely affecting system utility and user comfort. Additionally, existing portable negative-pressure wound dressing systems do not utilize absorbent materials and additional wound dressing components arranged to maximize the management of wound exudate within the dressing. Thus, there exists a need for a portable exudate management system that incorporates these, and other, features. The present disclosure seeks to overcome limitations and other drawbacks of the prior art, and to provide new features not heretofore available. A full discussion of the features and advantages of the present disclosure is deferred to the following detailed description, which proceeds with reference to the accompanying drawings.

SUMMARY

In one implementation, the present disclosure provides a negative pressure wound dressing for use in applying negative pressure to a wound comprising: an absorbent layer capable of absorbing exudate from the wound and allowing the passage of fluid through it; an outer cover layer covering the side of the absorbent layer furthest from the wound, the cover layer adapted to enable negative pressure to be applied at the wound and having a port; a conduit having a proximal end attached to the port and a distal end, the dressing provided with a pathway for fluid from the wound, through the absorbent layer, the port and to the distal end of the conduit; and an indicator means positioned in the pathway at a location between the absorbent layer and the distal end of the conduit, the indicator means capable of absorbing exudate to indicate the presence of exudate at the side of the absorbent layer furthest from the wound.

In a further implementation, the present disclosure provides a negative pressure wound dressing for use in applying negative pressure to a wound comprising: an absorbent layer capable of absorbing exudate from the wound and allowing the passage of fluid through it; an outer cover layer covering the side of the absorbent layer furthest from the wound, the cover layer adapted to enable negative pressure to be applied at the wound and having a port; a conduit having a proximal end attached to the port and a distal end, the dressing provided with a pathway for fluid from the wound, through the absorbent layer, the port and to the distal end of the conduit; an indicator means positioned in the pathway at a location between the absorbent layer and the distal end of the conduit, the indicator means capable of absorbing exudate to indicate the presence of exudate at the side of the absorbent layer furthest from the wound; and a source of negative pressure connected to the distal end of the conduit.

Preferably the source of negative pressure is capable of generating a minimum of 75 mmHg and a maximum of 125 mmHg at the wound.

In some implementations of the disclosed subject technology, a wound exudate management system is provided. In one embodiment, the wound exudate management system comprises a pump for generating negative pressure, a dressing for covering and protecting a wound, the dressing comprising an adhesive layer for adhering the dressing adjacent the wound, a wound contact layer for contacting the wound, a pressure dispersion layer, a plurality of layers of absorbent material disposed between the wound contact layer and the pressure dispersion layer, and a backing layer having a first surface and a second surface, the first surface of the backing layer being adjacent, and in contact with, the pressure dispersion layer and the adhesive layer, a pressure tube having an interior lumen, the pressure tube disposed between the pump and the dressing such that the pump and the dressing are in fluid communication via the interior lumen, and, a flexible connector connected to the second surface of the backing layer.

The disclosed technology further relates to a dressing for covering and protecting a wound. The disclosed technology further relates to a wound exudate management system, comprising: a dressing for covering and protecting a wound, the dressing comprising: a wound contact layer, the wound contact layer having a first surface and a second surface, the wound contact layer further having a peripheral region and a central region, wherein the first surface of the wound contact layer contacts the wound when the dressing is adhered to skin adjacent the wound, a pressure dispersion layer having a peripheral region and a central region, a plurality of layers of absorbent material disposed between the second surface of the wound contact layer and the pressure dispersion layer, and, an envelope formed by joining the peripheral region of the pressure dispersion layer with the peripheral region of the second surface of the wound contact layer, the plurality of layers of absorbent material being disposed substantially within an interior cavity of the envelope. Alternately, an envelope may be formed by joining the peripheral region of a thermoplastic spun lace layer connected to the pressure dispersion layer with the peripheral region of a nonwoven spun lace layer connected to the second surface of the wound contact layer, such that the plurality of layers of absorbent material are disposed substantially within an interior cavity of the envelope.

The disclosed technology further relates to a wound exudate management system further comprising a thermoplastic spun lace layer connected to the pressure dispersion layer, and a nonwoven spun lace layer connected to the wound contact layer, and wherein the envelope is formed by joining peripheral portions of the thermoplastic spun lace layer and the nonwoven spun lace layer, wherein the interior cavity of the envelope is formed by the nonwoven spun lace layer and the thermoplastic spun lace layer, and wherein the plurality of layers of absorbent material are disposed substantially within an interior cavity of the envelope.

The disclosed technology further relates to a wound exudate management system, comprising: a dressing for covering and protecting a wound, the dressing comprising a wound contact layer, a backing layer and at least one layer of absorbent material layer between the wound contact layer and the backing layer, a flexible connector having an interior lumen, the flexible connector secured to the backing layer of the dressing, an indicator between the backing layer and the flexible connector, a tube having an interior lumen, the tube connected to the flexible connector, wherein the interior lumen of the flexible connector and the interior lumen of the tube are in fluid communication, and, a pressure conveyance member disposed within the interior lumen of the tube.

The disclosed technology further relates to a wound exudate management system, comprising: a pump for generating negative pressure, a dressing for covering and protecting a wound, the dressing comprising a wound contact layer, a backing layer and at least one layer of absorbent material between the wound contact layer and the backing layer, a tube connecting the pump and the dressing, the tube having an interior lumen for placing the pump and the dressing in fluid communication via the interior lumen, and, a one-way valve in-line between the pump and the dressing to maintain a negative pressure within the dressing when the pump is disconnected from the tube.

The disclosed technology further relates to a wound exudate management system, comprising: a pump for generating negative pressure, a dressing for covering and protecting a wound, a tube including an interior lumen, the tube disposed between the pump and the dressing such that the pump and the dressing are in fluid communication via the interior lumen of the tube, and, a plurality of layers of absorbent material disposed in the dressing, wherein the absorbent material has fibers that swell upon contact with wound exudate to manage a flow of wound exudate through a portion of the dressing.

In any of the wound exudate management systems, the system may be adapted to allow for fluid communication between the wound and a negative pressure source, such as a pump. Typically, a fluid communication pathway is provided from the wound, through the wound contact layer and through one or more layers of absorbent material disposed in the dressing, to the negative pressure source. The fluid communication pathway may extend though an opening in the backing layer to the interior lumen of a tube, optionally via the interior lumen or conduit of a flexible connector. Where an indicator such as an absorbent indicator member is present, the fluid communication pathway may also extend through the indicator.

Typically, the flexible connector is elongate with an interior lumen or conduit that runs parallel to the longitudinal axis of the flexible connector, wherein the flexible connector is attachable to the opening in the backing layer of the dressing in an orientation such that the longitudinal axis of the flexible connector is substantially parallel to the plane of the backing layer. The flexible member may comprise a head portion for securement to the backing layer via adhesive or other means. Typically, the fluid communication pathway extends from the interior lumen or conduit of the flexible connector through the opening in the backing layer in a direction substantially perpendicular to the longitudinal axis of the flexible connector. Once secured, a fluid-tight seal may be formed between the flexible connector and the backing layer.

In any of the above embodiments, the presence of an indicator means may have the advantage that the user or caregiver is given an indication of the need to change the dressing. The indicator means allows the user or caregiver to change the dressing and prevent fouling of the pump. The presence of exudate at the side of the absorbent layer furthest from the wound occurs when the absorbent layer has absorbed significant quantities of exudate. If the indicator means is located in the conduit of the dressing and is triggered by the absorption of exudate, exudate is present not only at the side of the absorbent layer furthest from the wound but has also been drawn out past the cover layer and into the conduit. It gives a forewarning to the user or caregiver that the fluid handling capacity of the dressing has been or shortly will be reached and that dressing change is advisable. The indicator means can give an indication that the dressing has reached its fluid handling capacity and that there is potential for exudate to be drawn from the dressing, into the conduit and eventually into the pump which is undesirable.

The indicator means may be visual or may result in an audible alarm or other signal. Preferably the indicator means is visual and is located so that it is visible to the user of the dressing. For example, the visual indicator means may be located in the port in the cover layer or it may be located in the conduit or in both the port and conduit. Similarly, in the wound exudate management systems, the visual indicator means may be located to traverse the opening in the backing layer and/or be located in the interior lumen or conduit of the flexible connector. Preferably the visual indicator means is a gelling absorbent which visually indicates that it has absorbed exudate by forming a gel. If the exudate is coloured then the gel will also be coloured and add to the visual indication. Alternatively the visual indicator means may indicate that it has absorbed exudate by changing colour for instance by activation of a dye in the indicator means.

Preferably the indicator means is provided by gel-forming fibres. By gel forming fibres is meant hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd. In this way, the indicator means can be provided by a layer of gel forming fibres preferably located in the port of the cover layer or as a layer of fibres in the conduit. When present in the conduit, the layer of fibres can also serve to keep the conduit open to the passage of fluid in the event that the conduit is kinked or otherwise restricted by being lain on or leaned on by the user. The carboxymethylated cellullosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

The absorbent layer of the dressing is capable of absorbing exudate from the wound and allowing the passage of fluid through it. Although the absorbent layer can comprise any absorbent capable of absorbing exudate while allowing the passage of fluid through it, such as a foam, sponge or fibre-based material, preferably the absorbent layer is provided by gel forming fibres of the same type or of a different type as those used in the indicator means. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics and more preferably are of the type used in the indicator means. The gel forming fibres are preferably lightly carboxymethylated in order to reduce the tendency of the absorbent layer to gel block and block the pathway for fluid from the wound, through the absorbent layer, the port and to the distal end of the conduit.

Preferably the absorbent layer is provided with fenestrations to aid the application of negative pressure to the wound and maintain the pathway for fluid from the wound, through the absorbent layer. Typically, however, fenestrations are only provided in internal absorbent layers. External absorbent layers, including those in direct contact with the wound, generally do not have mechanically added fenestrations, however, they do have openings between the fibres.

Although the absorbent layer can be in direct contact with the wound, preferably the dressing comprises a wound contact layer, positioned between the wound and the absorbent layer. The wound contact layer is capable of absorbing exudate from the wound and transmitting it to the absorbent layer. Like the absorbent layer, the wound contact layer is capable of allowing the passage of fluid through it so that negative pressure may applied to the wound and the pathway for fluid from the wound and to the distal end of the conduit may be maintained.

Preferably the wound contact layer comprises gel-forming fibres of the same or a similar type to those comprising the absorbent layer but the wound contact layer may be strengthened to increase its integrity and that of the dressing. For example the wound contact layer may be of the type described in EP 190401 1 and comprise gel-forming fibres in the form of a mat with lines of longitudinal stitching made of cellulose or nylon or polyolefin yarn to increase the integrity of the layer. Preferably the wound contact layer is porous to maintain the pathway for fluid from the wound to the distal end of the conduit.

The outer cover layer of the dressing is a bacterial and viral barrier layer which preferably resists the ingress of liquid and air but allows moisture vapour transmission. In this way the outer cover layer enhances the overall fluid handling capacity of the dressing by allowing for the escape of moisture vapour through the cover while enabling the application of negative pressure to the wound. The outer cover layer is for instance a layer having a MVTR of at least 10,000 g m-2 per 24 hours or in the range of from 10,000 gm-2 to 50,000 g m-2 per 24 hours measured by the method described in BS EN 13726-2 2002 "Test methods for primary wound dressings Part 2 Moisture vapour transmission rate of permeable film dressings". The cover layer may be in the form of a film of polyurethane, for example Epurex 912 T/129 manufactured by Covestro or Inspire 2350 manufactures by Coveris or Medifilm 426 manufactured by Myl an.

The cover layer is provided with a port for connection to the conduit. The port is preferably located in that part of the cover layer that overlies the absorbent layer but towards the periphery of the absorbent layer so that it is not directly in vertical alignment with the centre of the dressing (or the wound when in use). This assists in the spread of exudate across the full extent of the absorbent layer.

The conduit of the dressing is preferably a transparent passageway secured to the outside of the cover layer at the proximal end of the conduit so as to surround the port in the cover layer from above. In this manner if the visual indicator is located in the port in the cover layer and/or in the conduit itself, the visual indicator may be seen by the user. Similarly, where the wound exudate management systems comprise a flexible connector, the flexible connector may be partially or entirely transparent so as to allow the visual indicator to be seen by the user. Typically the head of the flexible connector is transparent. The conduit of the dressing may comprise a connector, at its distal end, for connecting the dressing to a source of negative pressure, for example a pump. Preferably the connector is a luer lock to facilitate secure connection to the pump and to maintain the negative pressure on the wound while the pump is temporarily disconnected. The connector preferably comprises a one way lock to assist in the maintenance of negative pressure. The visual indicator may be located in the conduit and can be in the form of a knitted cylinder, or the like, of gel forming fibres. To resist collapse, the conduit may comprise an internal cylinder of nylon fibres to maintain openness of the conduit to fluid.

The dressing may further comprise a distribution layer, e.g., a pressure distribution layer, located between the absorbent layer and the outer cover layer which is gas and liquid permeable and particularly moisture vapour permeable and serves to aid access of exudate to a greater area of the absorbent layer by allowing it to spread under the distribution layer. The distribution layer also serves to even out the negative pressure applied to the wound over the whole dressing. The distribution layer preferably distributes exudate and negative pressure over the dressing. In this way, uptake of exudate by the absorbent layer is maximised before the exudate leaves the absorbent layer and activates the indicator means and the transfer of negative pressure to the wound is optimised. The distribution layer is preferably a foam layer such as a polyester foam of the type XD4200AS manufactured by Caligen or another suitable reticulated foam.

The dressing may also comprise additional optional layers such as an adhesive layer for adhering the dressing to the skin surrounding the wound to form a fluid tight seal. The adhesive layer may be applied to the side of dressing closest to the wound and may be provided with perforations to assist transport of exudate and fluid through the dressing. The adhesive layer may also be applied to any of the other layers to provide an island configuration such as to the cover layer.

It is understood that other embodiments and configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

To understand the present disclosure, it will now be described by way of example, with reference to the accompanying drawings in which implementations of the disclosures are illustrated and, together with the descriptions below, serve to explain the principles of the disclosure.

DETAILED DESCRIPTION

Figure 1:
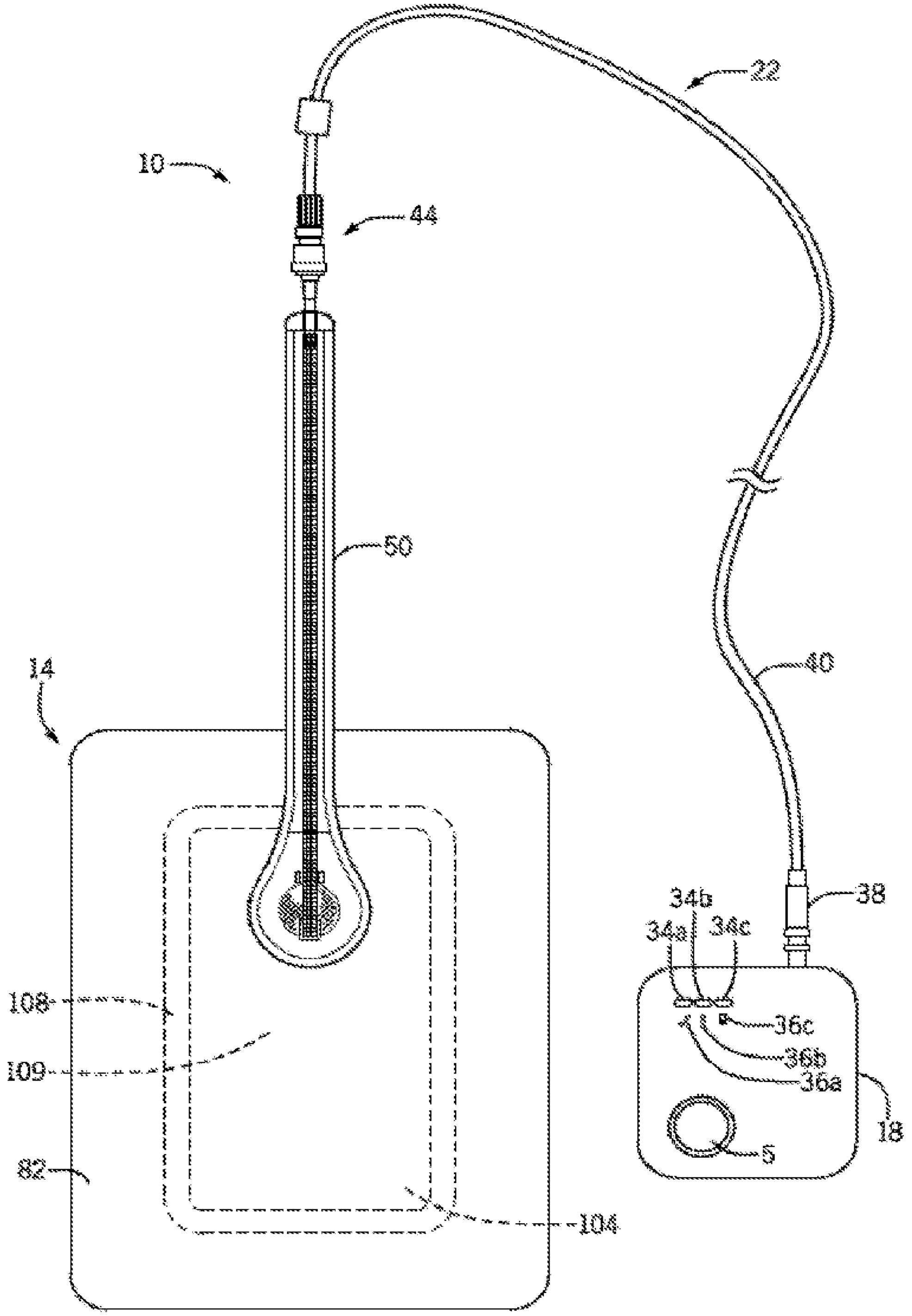
FIG. 1 is a top view of a wound exudate management system according to exemplary implementations of the present disclosure, in particular showing a pump, a dressing and a tube, among other features.
Figure 2:
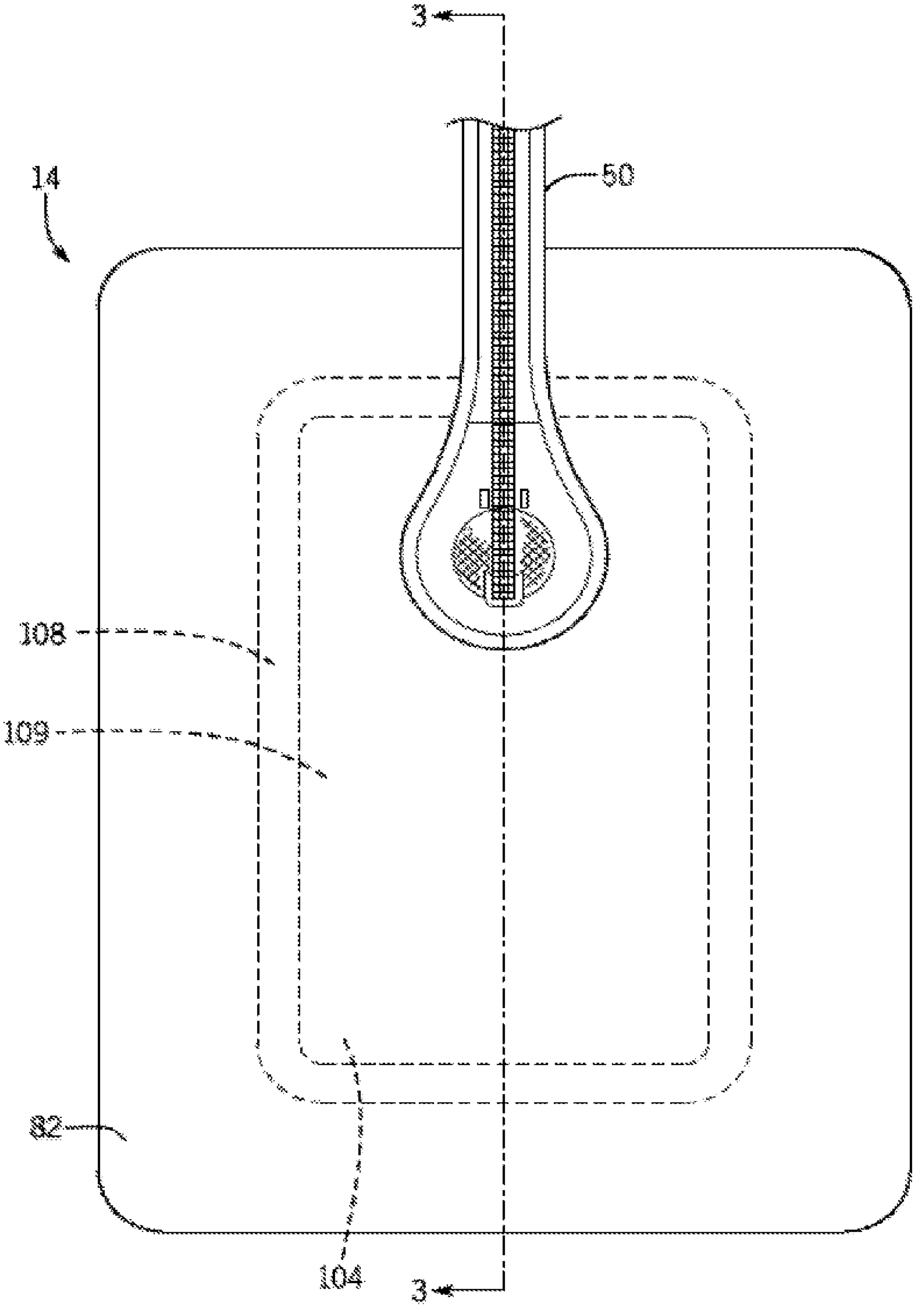
FIG. 2 is a top view of a wound exudate management system according to exemplary implementations of the present disclosure, in particular showing a dressing and a portion of a flexible connector of the wound exudate management system.

While the wound exudate management system discussed herein may be implemented in many different forms, there is shown in the drawings, and will herein describe in detail, preferred implementations with the understanding that the present description is to be considered as an exemplification of the principles of the wound exudate management system and is not intended to limit the broad aspects of the disclosure to the implementations illustrated.

Referring now to the figures, and specifically to FIG. 1, one embodiment of a wound exudate management system 10 is shown. The wound exudate management system 10 of this embodiment has a wound dressing 14, a pump 18 and a tube 22 (also referred to as a pressure tube 22). Generally, the wound exudate management system 10 facilitates wound healing and wound protection. The dressing 14 is applied to the skin of a user, as will be described below, and the system 10 utilizes negative pressure generated by the pump 18 to aid wound healing. The dressing 14 and the pump 18 are fluidly connected via the tube 22. Negative pressure generated by the pump 18 is communicated to the dressing 14 by the tube 22, thereby enabling the dressing 14 to employ negative pressure for enhanced wound healing.

In various embodiments, the pump 18 operates to generate negative pressure in response to a variety of user inputs. In one embodiment, a user control 30 for the pump 18 is disposed on the pump 18 and/or remote to the pump 18. The user control 30 may be one or more of a button, switch, lever, sensor or any other control device. It is to be understood that any common user control 30 is within the scope of this disclosure. The pump 18 may also have one or more indicators 34*a*, 34*b*, 34*c* disposed on the pump 18 for apprising the pump user of a current operational status, condition, battery life, etc. of the pump 18. The indicators 34*a-c* may be lights including Light-Emitting Diodes (LEDs), however any other type of indicator may be used such as a speaker for generating an audible sound or a motor with a radially asymmetric flywheel for generating a vibration. Instructional indicia 36*a*, 36*b*, 36*c* may be associated with one or more of the indicators 34*a-c* for apprising a user of the significance of an operation of a particular indicator 34*a-c*. In some implementations, however, the pump 18 operates without a user input and generates negative pressure in response to a timer, remote signal, sensor reading or other stimulus.

In one embodiment, prior to operation of the pump 18, the indicators 34*a-c* for the pump 18 are preferably not illuminated. In such a state, the pump 18 is generally not generating negative pressure, which may correspond to the pump 18 being in an off condition. Further, in one embodiment, when all of indicators 34*a-c* transition to an illuminated state, the pump 18 is preferably in a ready state and is ready for use. Further, in one embodiment, when one indicator 34*a* remains in an illuminated state and the remaining indicators 34*b* and 34*c* transition to a non-illuminated state, this is an indication that the pump 18 is in an operating state. Normal operation of the pump 18 may include the generation of negative pressure, alternating periods of negative pressure generation, and/or no generation of negative pressure. The pump 18 may transition between one or more of the off condition, ready state and operating state as a result of manipulation of the user control 30. Manipulation of the user control 30 to change the pump state may include and/or require manipulation of the user control 30 for a predetermined amount of time.

In the operational state, in a preferred embodiment the pump 18 generates a minimum pressure of 75 mmHg at the wound and a maximum pressure of 125 mmHg at the wound, however, alternate pressures may be generated by the pump 18. In one embodiment, the pump 18 generates negative pressure until a first pressure threshold is reached. The first pressure threshold may be, for example, a value between 75 mmHg and 125 mmHg, inclusive. The pump 18 may then refrain from generating negative pressure until a second threshold pressure is reached, at which point the pump 18 may generate negative pressure until the first pressure threshold is again reached. Alternate operations of the pump are allowable.

In one embodiment, as shown in FIG. 1, the pump 18 is connected to the pressure tube 22 with a pump connector 38. The pump connector 38 may allow for selective separation of the pump 18 and the tube 22.

Figure 7:
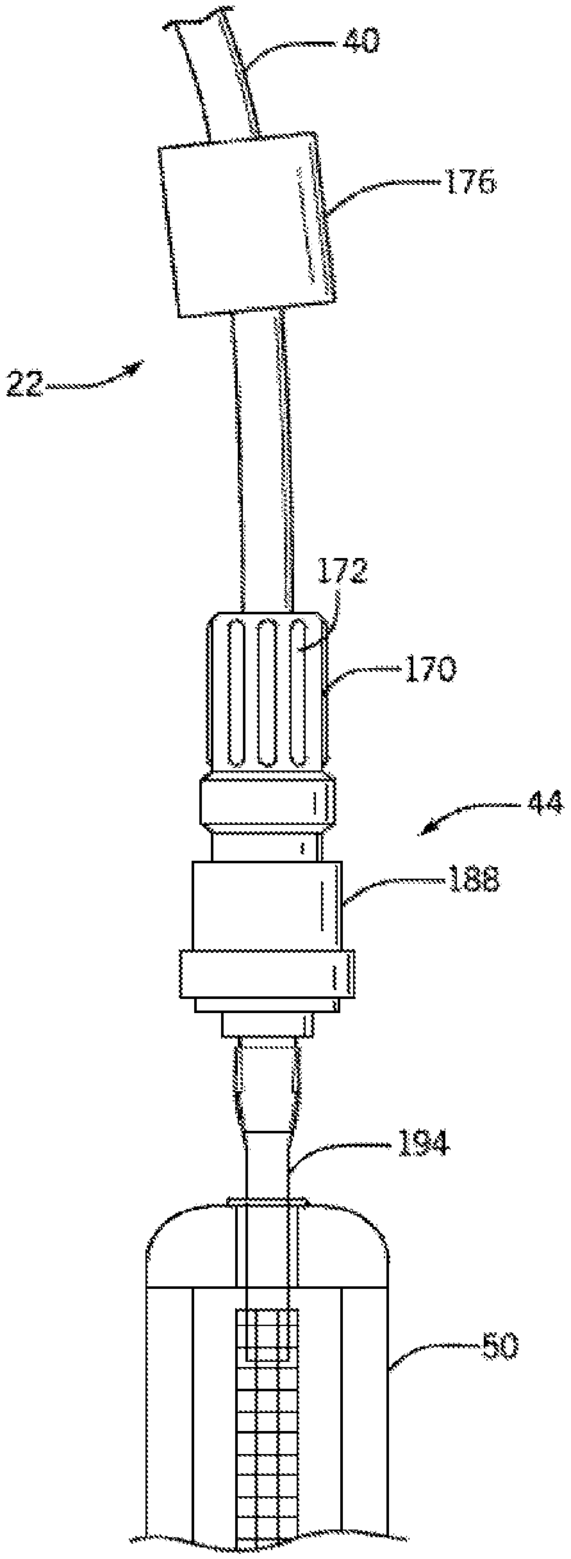
FIG. 7 is a top view of a releasable connector of a wound exudate management system according to exemplary implementations of the present disclosure, in particular showing the releasable connector in a connected state.
Figure 8:
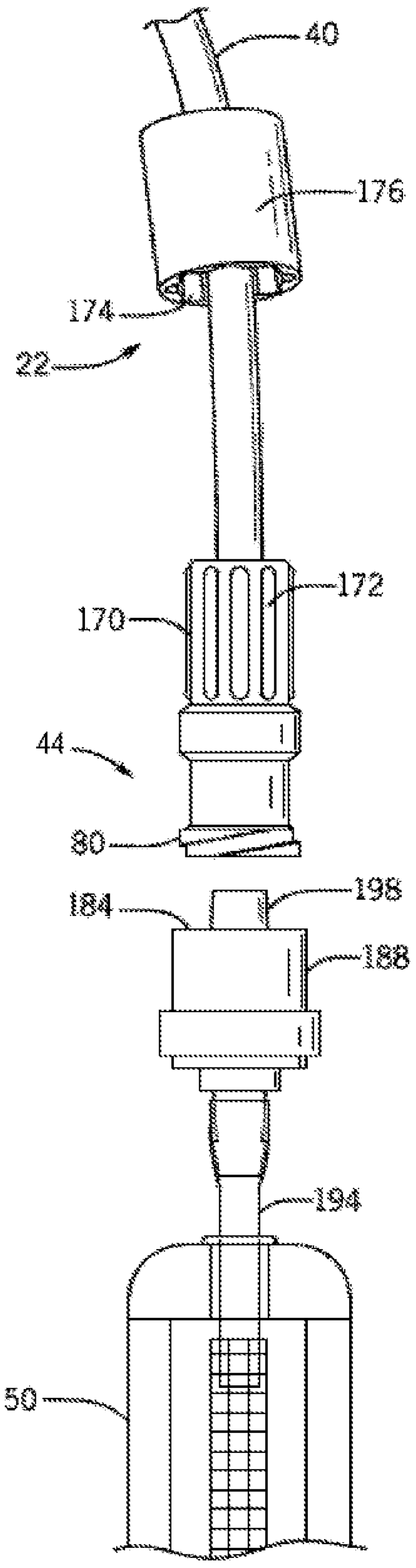
FIG. 8 is a top view of the releasable connector of FIG. 7, in particular showing the releasable connector in a detached state.

In one embodiment, the tube 22 comprises a distal tube portion 40 and a proximal tubular portion 42. The proximal tubular portion 42 may be an extension of the flexible connector 50. A separable connector 44 may join the distal tube portion 40 and the proximal tubular portion 42, as shown in FIGS. 7 and 8. The pump connector 38 connects one end of the tube 22, and preferably the distal tube 40 portion of the tube 22, to the pump 18, as shown in FIG. 1. However, in an alternate embodiment, not shown, the pump connector 38 may connect the proximal tubular portion 42 to the pump 18. In one embodiment, the distal tube portion 40 forms a portion of the pressure tube 22 and may be flexible, transparent, partially-transparent, and/or formed from a polymer, metal, metal alloy or any other suitable material.

Figure 3A:
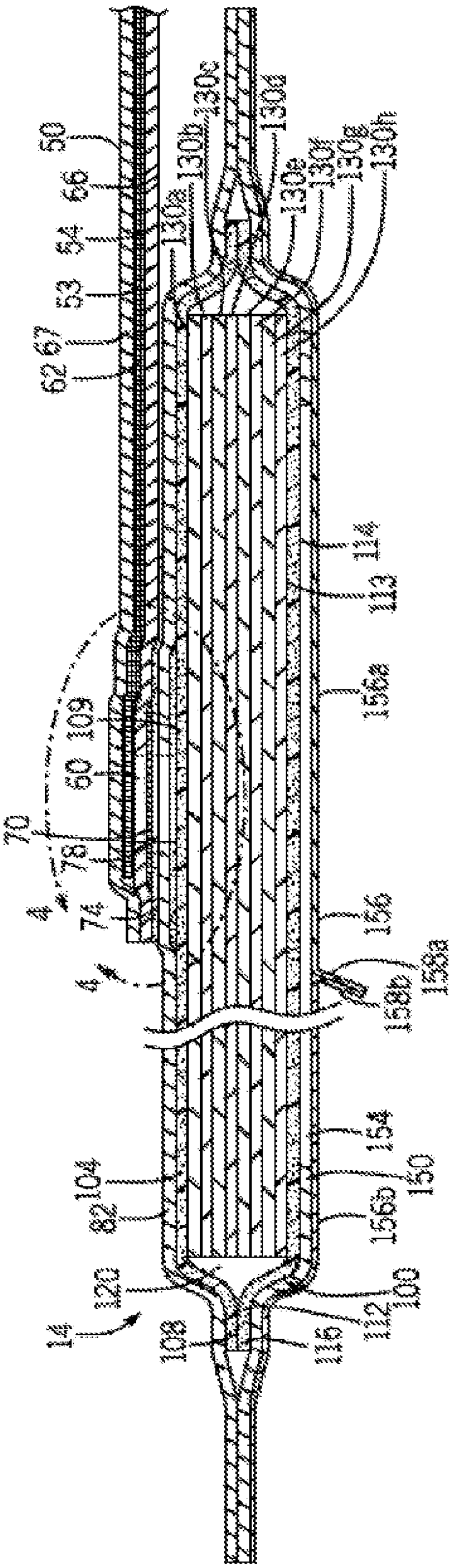
FIG. 3A is a cross-sectional view about line 3-3 of FIG. 2 of a wound exudate management system according to exemplary implementations of the present disclosure, in particular showing a dressing, a portion of a flexible connector and various constituent elements of the dressing.
Figure 4:
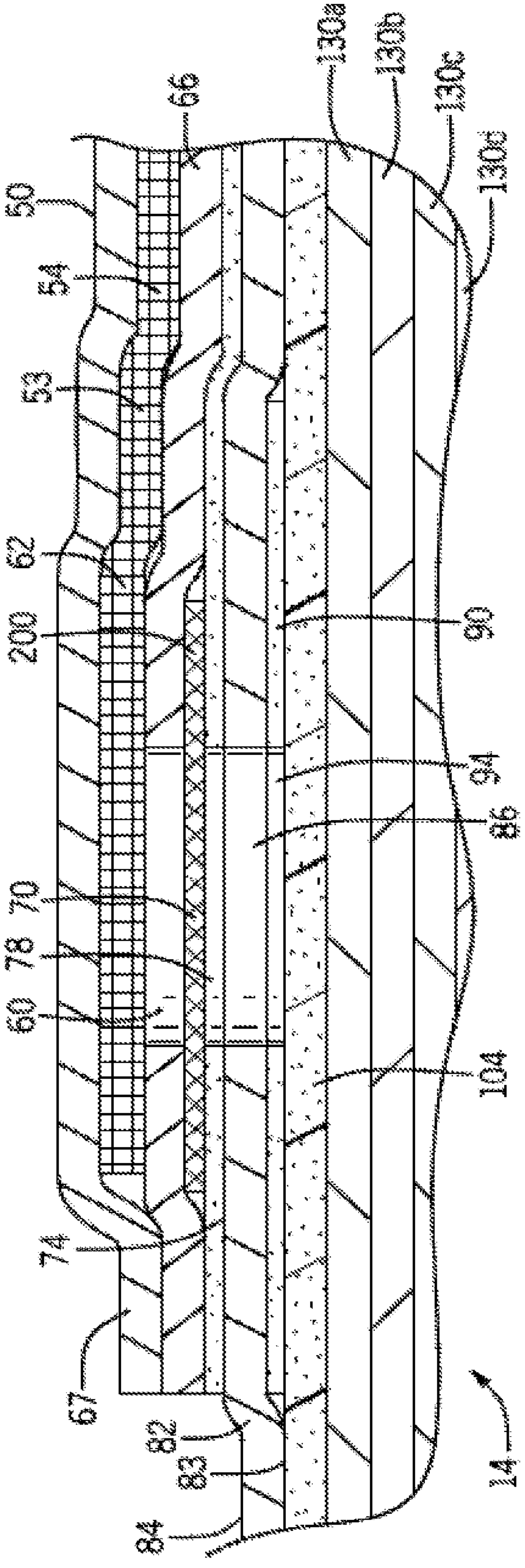
FIG. 4 is an enlarged cross-sectional view of the wound exudate management system of FIG. 3A, in particular illustrating the region indicated by arrow 4-4.

Turning to FIGS. 3A and 4, in one embodiment the flexible connector 50 is structurally connected to the dressing 14, and further includes a flexible connector lumen 54. The flexible connector lumen 54 is disposed within the flexible connector 50 along a portion, or all, of the flexible connector 50 and enables fluid communication between the pump 18 and the dressing 14. A flexible connector aperture 60 enables fluid communication between the flexible connector lumen 54 and the dressing 14. The flexible connector 50 may include a lower flexible connector portion 66 and an upper flexible connector portion 67. The lower flexible connector portion 66 and the upper flexible connector portion 67 may be joined by welding, adhesives or any other joining technique to form the flexible connector 50. The flexible connector 50 may preferably be formed from polyvinyl chloride, polyurethane or any other suitable material. In one embodiment the flexible connector 50 has a generally planar exterior surface.

In one embodiment, a pressure conveyance structure 62 is disposed within the flexible connector lumen 54. The pressure conveyance structure 62 enables the flexible connector 50 to convey fluid flow and/or pressure within the flexible connector lumen 54 without collapsing when the flexible connector 50 is made of a thin-walled flexible material, thereby enabling the dressing 14 to experience or exhibit negative pressure generated by the pump 18. The pressure conveyance structure 62 may include various materials including, but not limited to, nylon. Further, the pressure conveyance structure 62 may be comprised of a lattice structure 53. The shape, material and arrangement of the pressure conveyance structure 62 enables continued fluid flow along the flexible connector 50 that may otherwise be hindered by the shape, flexibility, material or arrangement of the flexible connector 50 in light of negative pressure generated by the pump 18 and in light of general wound exudate management system 10 use and positioning.

As best shown in FIGS. 3A, 4 and 5, the dressing 14 preferably includes an indicator 70, which in one embodiment is an upper absorbent indicator member 70 formed of an absorbent material. The indicator 70 may produce a signal, such as a visual, audible, vibrational, etc. signal. When the indicator 70 is made of an absorbent material the absorbent material may include gel-forming fibers, which may be hygroscopic fibers that become moist, slippery or gelatinous upon the intake of wound exudate or other fluids. The gel-forming fibers may retain their structural integrity upon absorption of exudate or they may lose their fibrous form and become an amorphous or structure-less gel. The gel-forming fibers are, in some implementations, sodium carboxymethylcellulose fibers, chemically modified cellulosic fibers, alkyl sulphonate modified cellulosic fibers such as those described in WO2012/061225, pectin fibers, alginate fibers, chitosan fibers, hyaluronic acid fibers, other polysaccharide fibers or fibers derived from gums.

The cellulosic fibers exemplarily have a degree of substitution of at least 0.05 carboxymethyl groups per glucose unit. The gel-forming fibers may have an absorbency of at least 2 grams 0.9% saline solution per gram of fiber (as measured by a free swell method) but less than 30 grams 0.9% saline solution per gram of fiber.

The gel-forming fibers are preferably chemically modified cellulosic fibers in the form of a fabric and in particular carboxymethylated cellulose fibers as described in PCT WO00/01425 to Azko Nobel UK Ltd. The carboxymethylated cellullosic fabrics exemplarily have a degree of substitution between 0.12 to 0.35 as measured by IR spectroscopy (as defined in WO00/01425) and further may have a degree of substitution of between 0.20 and 0.30. The carboxymethylated cellullosic fabrics may be formed by carboxymethylating a woven or nonwoven cellulosic fabric such that absorbency is increased. The fabric may have an absorbency of between 10 g/g of sodium/calcium chloride to 30 g/g of sodium/calcium chloride as measured by the method described in BS EN 13726-1 (2002) "Test methods for primary wound dressings", section 3.2 "Free swell absorptive capacity." Some fabrics have an absorbency of 15 g/g to 25 g/g or 15 g/g to 20 g/g of sodium/calcium chloride. The gel-forming fibers may be lightly carboxymethylated to reduce a tendency of the absorbent material to gel block and block a fluid pathway from the wound and through the dressing 14.

The cellulosic fabric may consist solely of cellulosic fiber but may also contain non-cellulosic textile fibers or gel-forming fibers. The cellulosic fiber may be of known kind and may include continuous filament yarn and/or staple fiber. The carboxymethylation may be performed by contacting the fabric with an alkali and a carboxymethylating agent, such a chloracetic acid in an aqueous system. The fabric may be of a non-woven type, and may further be hydroentangled and thus comprise a series of apertures on a microscopic scale.

The absorbent material may also comprise any absorbent material capable of absorbing exudate while allowing the passage of fluid therethrough, such as a foam, sponge or fiber-based material. [0059] The upper absorbent indicator member 70 is preferably above the backing layer 82 and may be adjacent, joined to and/or in contact with the flexible connector 50 and may also be adjacent the flexible connector aperture 60. As best shown in FIG. 4, in one embodiment a first side of an upper adhesive 74 is adhered to both the upper absorbent indicator member 70 and the lower flexible connector portion 66 of the flexible connector 50. The lower flexible connector portion 66 is preferably adhered to a portion of the first side of the upper adhesive 74 radially outward from a portion of the upper adhesive 74 to which the upper absorbent indicator member 70 is adhered. The upper adhesive 74 also has an upper adhesive aperture 78 extending from the first side of the upper adhesive 74 to a second side of the upper adhesive 74 and arranged to be adjacent the upper absorbent indicator member 70 to limit interference with the vacuum effect of the negative pressure draw through the upper absorbent indicator member 70.

In one embodiment a backing layer 82 is disposed between both the indicator member 70 and the flexible connector 50 and the plurality of absorbent layers of the dressing 14. In one embodiment the backing layer 82 is disposed below the upper adhesive 74. The backing layer 82 preferably has a backing layer aperture 86 disposed through the backing layer 82, and extending from a first surface 83 of the backing layer 82 to a second surface 84 of the backing layer. Accordingly, in one embodiment the upper adhesive 74 is provided adjacent the second surface 84 of the backing layer 82. In assembly, the aperture 86 of the backing layer 82 is provided adjacent the aperture 78 in the upper adhesive 74. In some implementations, the backing layer 82 is a bacterial and viral barrier layer which resists the ingress of liquid and air while allowing moisture vapor transmission. In this way, the backing layer 82 enhances an overall fluid handling capacity of the dressing 14 by allowing moisture vapor to escape through the backing layer 82 while enabling the application of negative pressure to the wound or dressing 14. The backing layer 82 may have a Moisture Vapor Transmission Rate (MVTR) of at least 10,000 $g/m^2$ per 24 hours or in the range of from 10,000 $g/m^2$ to 50,000 $g/m^2$ per 24 hours measured by the method described in BS EN 13726-2 2002 "Test methods for primary wound dressings Part 2 Moisture vapour transmission rate of permeable film dressings." The backing layer 82 may be partially or fully transparent. The backing layer 82 may be a layer, or film, of polyurethane, for example Epurex 912 T/129 manufactured by Covestro or Inspire 2350 manufactures by Coveris or Medifilm 426 manufactured by Mylan.

Figure 5A:
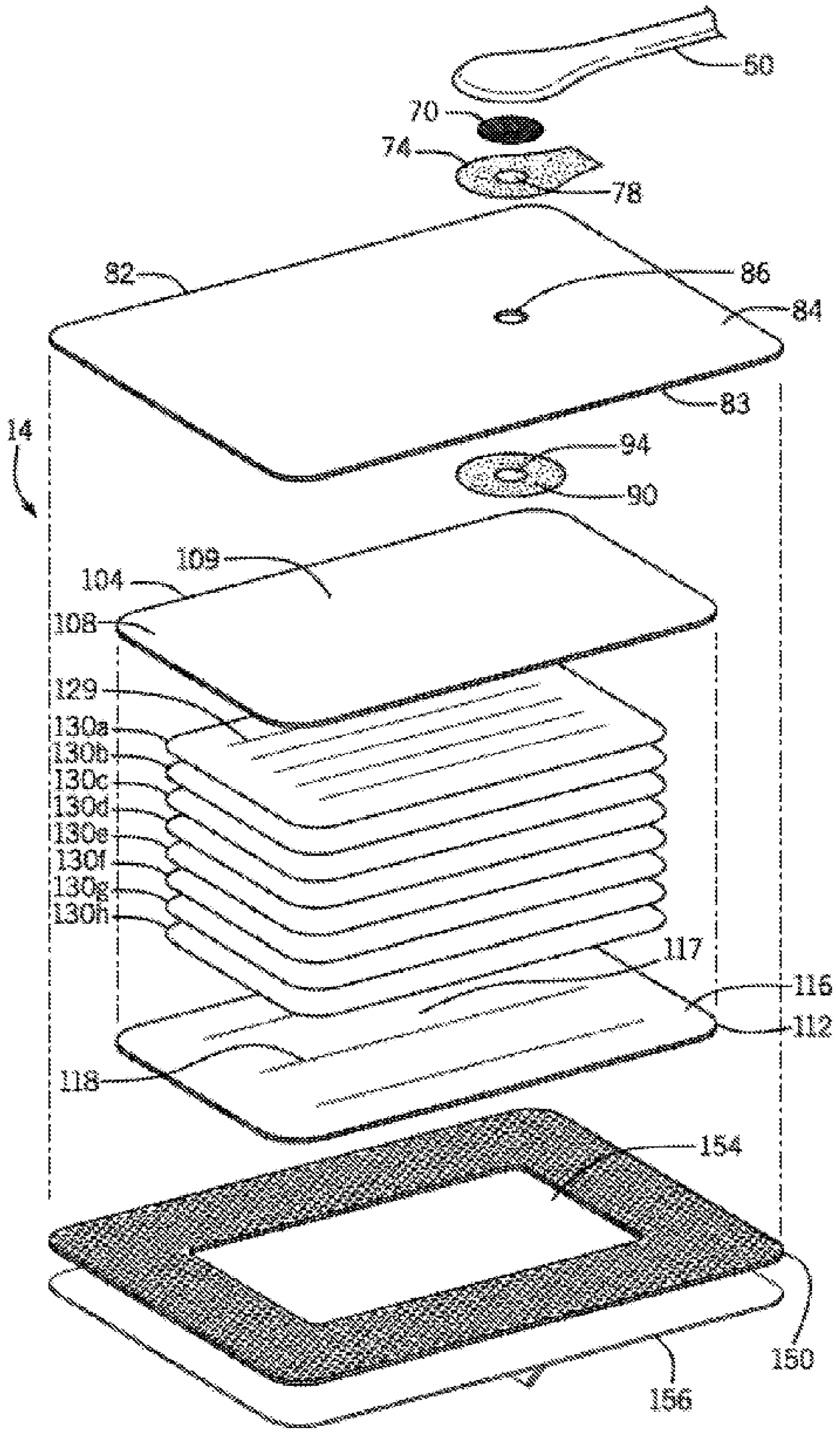
FIG. 5A is an exploded perspective view of a wound exudate management system according to exemplary implementations of the present disclosure.

As shown in FIGS. 4 and 5A, in one embodiment a layer of adhesive 90, referred to as the backing layer adhesive 90, is disposed adjacent the second surface 82*b* of the backing layer 82. The backing layer adhesive 90 includes a backing layer adhesive aperture 94 preferably extending through the backing layer adhesive 90 from a first surface of the backing layer adhesive 90 to a second surface of the backing layer adhesive 90. The aperture 94 in the backing layer adhesive 90 is preferably positioned adjacent the aperture 78 in the upper adhesive member 74. It is to be understood that in a preferred embodiment, the flexible connector aperture 60, upper absorbent indicator member 70, upper adhesive aperture 78, backing layer aperture 86 and backing layer adhesive aperture 94 are all arranged substantially concentric such that fluid flow is enabled from the flexible connector aperture 60, across the upper absorbent indicator member 70, and through the upper adhesive aperture 78, backing layer aperture 86 and backing layer adhesive aperture 94. Further, it is also to be understood that in a preferred embodiment the upper flexible connector portion 67, lower flexible connector portion 66, upper absorbent indicator member 70, upper adhesive 74, backing layer 82, and backing layer adhesive 90 are arranged sequentially in the wound exudate management system 10.

Referring to FIG. 3A, the dressing 14, in some implementations, includes an inner envelope structure 100. The inner envelope structure 100 preferably houses a plurality of layers of absorbent material to aid in exudate management. As best shown in FIGS. 3A, 4 and 5, in one embodiment the inner envelope structure 100 is defined by an upper envelope layer and a lower envelope layer. The upper envelope layer may have a peripheral section 108 and a central section 109. The peripheral section 108 of the upper envelope layer may also be referred to as the upper peripheral section 108, and the central section 109 of the upper envelope layer may also be referred to the upper central section 109. Similarly, the lower envelope layer may have a peripheral section 116 and a central section 117. The peripheral section 116 of the lower envelope layer may be referred to as the lower peripheral section 116, and the central section 117 of the lower envelope layer may be referred to as the lower central section 117.

Figure 3B:
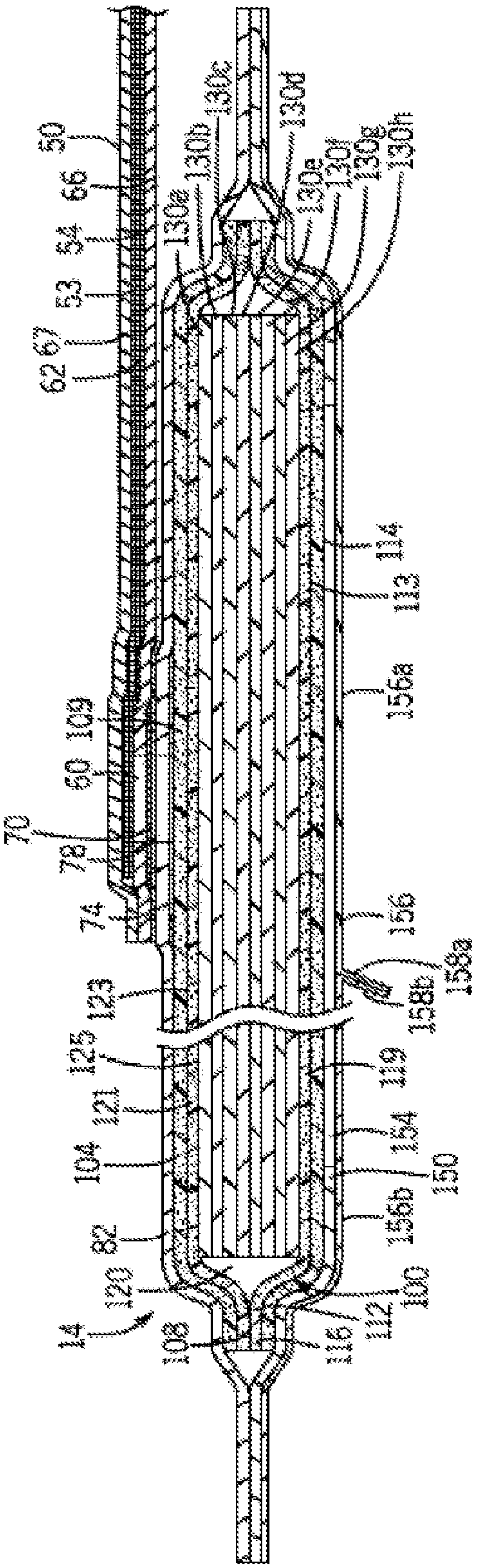
FIG. 3B is an alternate embodiment of a cross-sectional view about line 3-3 of FIG. 2 of a wound exudate management system showing a dressing, a portion of a flexible connector and various constituent elements of the dressing.
Figure 5B:
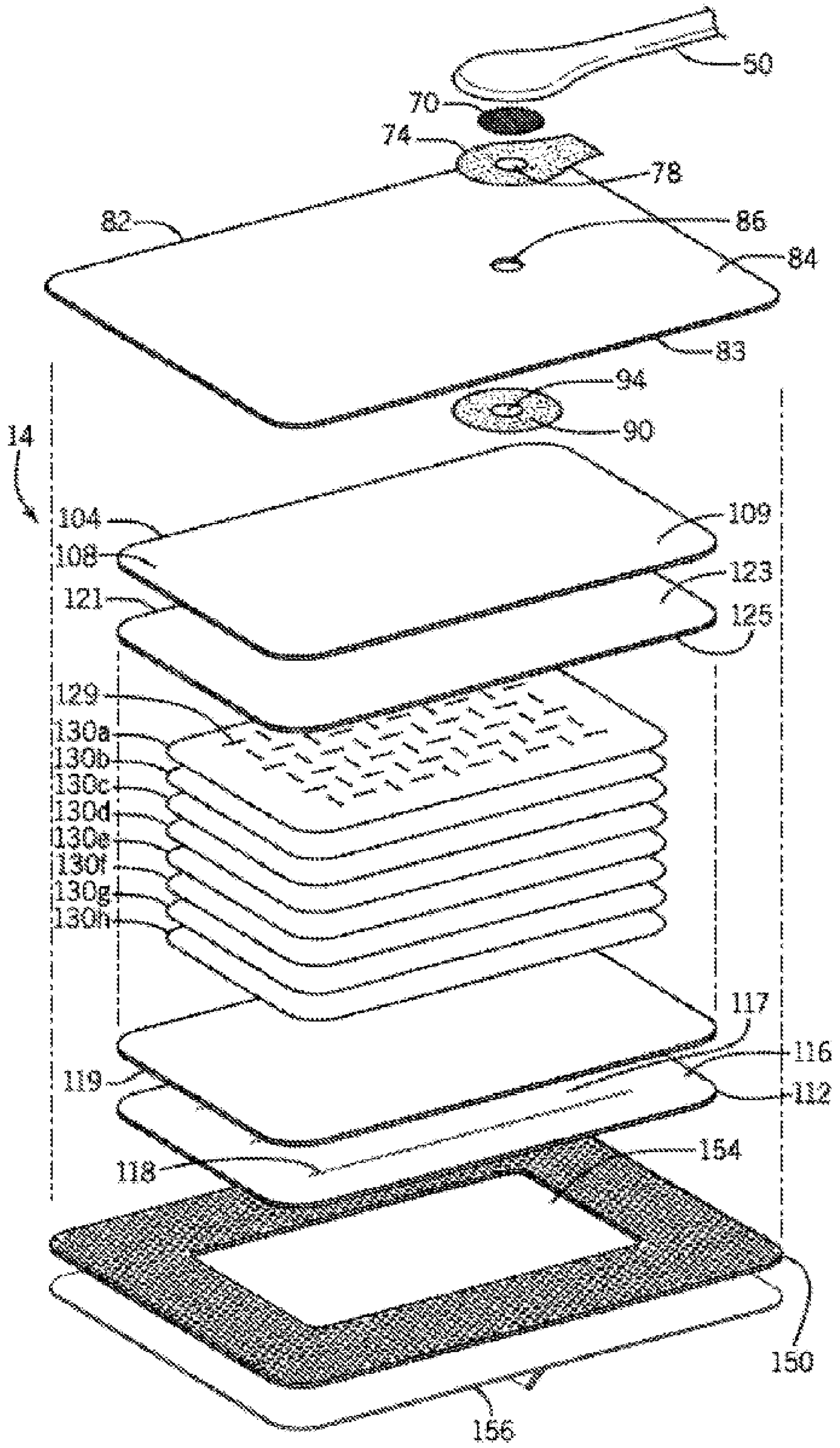
FIG. 5B is an alternate embodiment of an exploded perspective view of a wound exudate management system of the present disclosure.
Figure 6:
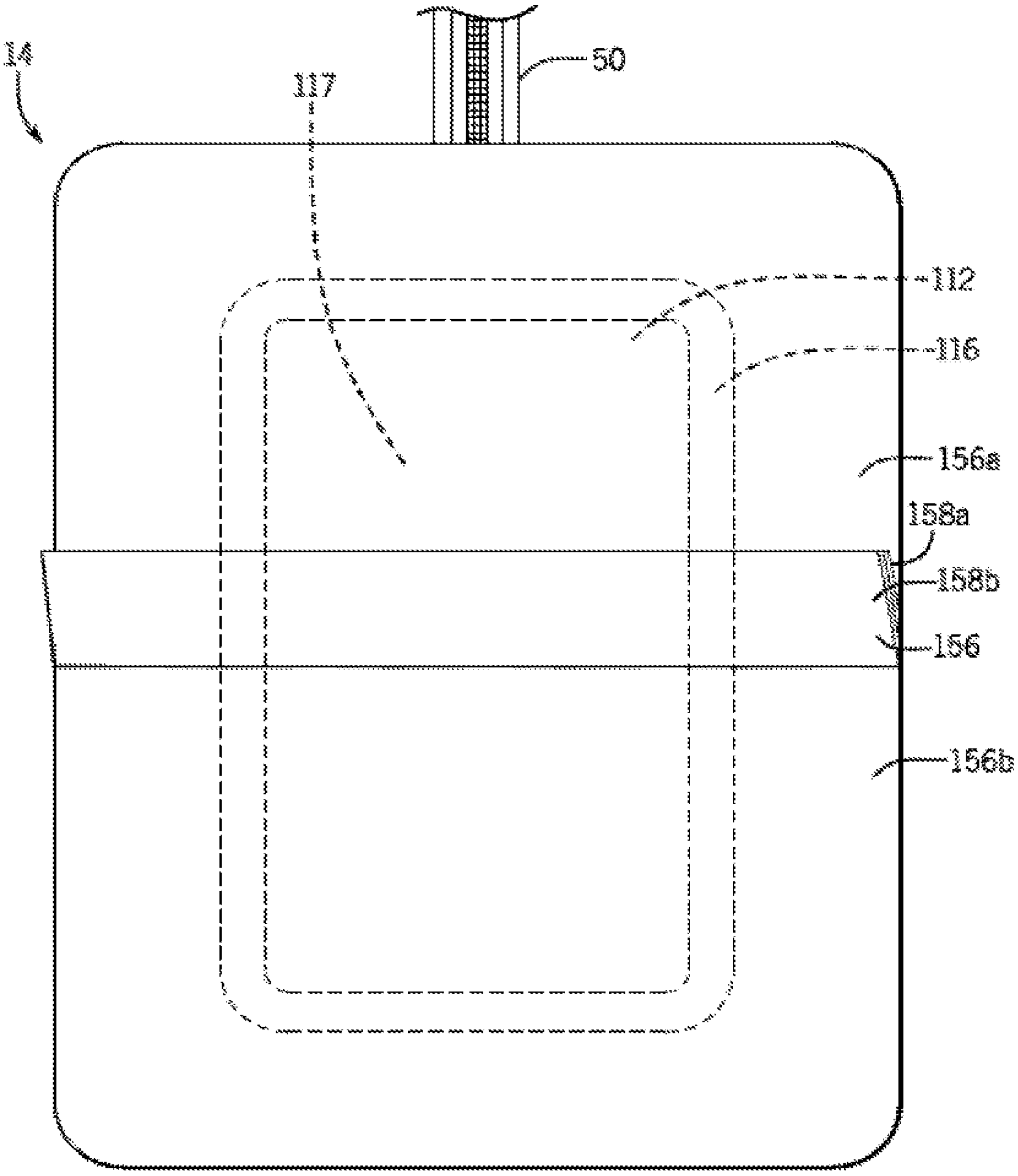
FIG. 6 is a bottom view of a wound exudate management system according to exemplary implementations of the present disclosure, in particular showing a removable cover and a portion of a flexible connector of the wound exudate management system.

An alternate embodiment of the dressing 14 of the wound management system 10 is shown in FIGS. 3B and 5B. In this alternate embodiment, a nonwoven spun lace layer 119 is preferably stitchbonded to the second surface 113 of the wound contact layer 112. In one embodiment a regenerated cellulose yarn is used for the stitchbonding. Further, in one embodiment the nonwoven spun lace material 119 may be comprised of an 80 gsm nonwoven layer comprising viscose fibers and polyester fibers in substantially equal portion, and preferably less than 5% acrylic co-polymer binder. Additionally, a thermoplastic spun lace layer 121, such as a polyamide layer, may be provided between the pressure dispensing layer 104 and the plurality of absorbent material layers 130. The thermoplastic spun lace layer 121 has a first surface 123 that may be heat bonded at its perimeter to the pressure dispersing layer 104, and a second surface 125 that may be similarly heat bonded at its perimeter around the plurality of absorbent material layers 130 to the nonwoven spun lace layer 119. Accordingly, the thermoplastic spun lace layer 121 and the nonwoven spun lace layer 119 form an inner enclosure or envelope around the absorbent material layers 130. The inner envelope or enclosure of this embodiment is defined by an upper envelope layer and a lower envelope layer. The upper envelope layer of this embodiment comprising the thermoplastic spun lace layer 121, and the lower envelope layer of this embodiment comprising the nonwoven spun lace material 119.

Accordingly, in one embodiment, as shown in FIG. 3A, the upper envelope layer is a pressure dispersing layer 104, and the lower envelope layer is a wound contact layer 112. In an alternate embodiment, as shown in FIG. 3B, the upper envelope layer is a thermoplastic spun lace layer 121 and the lower envelope layer is a non-woven spun lace layer 119.

In some implementations, the pressure dispersing layer 104, also referred to as the pressure distribution layer, serves to distribute pressure, or negative pressure, laterally across the pressure dispersing layer 104. The pressure dispersing layer 104 may be gas, liquid and moisture-vapor permeable and serves to aid exudate access to a greater portion of the dressing 14 by distributing negative pressure laterally over the dressing 14. In this way, uptake of exudate by the dressing 14 is maximized and a more uniform transfer of negative pressure to the wound, or dressing 14, is optimized. The pressure dispensing layer 104 may be formed from a foam such as a polyester foam of the type XD4200AS manufactured by Caligen, another suitable reticulated foam or a polyurethane foam.

In some implementations the wound contact layer 112 may be formed of an absorbent material. Further, the wound contact layer 112 may be comprised of a structurally reinforced material or structure to enhance the strength and physical properties of the lower envelope layer 112. For example, the wound contact layer 112 may be formed from carboxymethylated cellulose fibers. The structural reinforced material of the wound contact layer 112 may include stitching 118. In some implementations, the wound contact layer 112 is formed of an absorbent material that has reinforcing stitching 118, including reinforcing stitching 118 made of nylon. It is also understood that the pressure dispersing layer 104 and the wound contact layer 112 may be formed from any one of the absorbent materials described above.

The wound contact layer 112 has a first surface 114 and a second surface 113. In one embodiment, the first surface 114 of the wound contact layer 112 is an outer layer for contacting a wound of user when the dressing 14 is adhered to the skin of a user adjacent the wound. Further, in one embodiment, the second surface 113 of the wound contact layer 112 opposes the first surface 114, and the second surface 113 is an inner layer that is adjacent the plurality of absorbent material layers within the dressing 14, as described below.

The peripheral section 108 of the upper envelope layer 104 (i.e., in one embodiment the pressure dispersing layer 104) and peripheral section 116 of the lower envelope layer 112 (i.e., in one embodiment the wound contact layer 112) may be joined, as best shown in FIG. 3A. The upper peripheral section 108 and the lower peripheral section 116 may be joined by adhesives, welding, stitching or any other common joining method. The joining of the upper peripheral section 108 and the lower peripheral section 116 substantially forms the inner envelope 100 and further defines an envelope cavity 120 disposed within the envelope 100.

In a preferred embodiment, a plurality of absorbent material layers 130*a*, 130*b*, 130*c*, 130*d*, 130*e*, 130*f*, 130*g*, 130*h*, etc. are, in some implementations, disposed adjacent one another and substantially within the envelope cavity 120. In one embodiment there are eight layers of the absorbent material within the envelope cavity 120. In some implementations, the absorbent material layers 130*a-h* includes gel-forming fibers, such as those described above, and the gel-forming fibers may be sodium carboxymethylcellulose fibers. Further, the absorbent material layers 130*a-h* may include any of the absorbent materials, water-swellable fibers or gel-forming fibers as described above. For example, the absorbent material layers 130*a-h* may be formed from carboxymethylated cellulose fibers.

In some implementations, one or more of the absorbent material layers 130*a-h* includes one or more fenestrations 129, as shown in FIG. 5A. The fenestrations 129 may be slits or openings 129 in one or more directions on the absorbent material layers 130*a-h*, preferably in a direction planar to a longitudinal axis and transverse to a longitudinal axis of the absorbent materials, which aid in managing a flow of exudate through the various layers 130*a-h* of the dressing 14. In particular, the fenestrations 129 encourage or enable wound exudate to travel, or be absorbed, in a preferred direction. In some implementations, the fenestrations 129 encourage or enable wound exudate to travel laterally about each layer of the absorbent material layers, as opposed to axially from one layer to another. The fenestrations 129 may be formed mechanically, such as via cutting. The fenestrations 129 are preferably slits about 10 mm in length that may alternate vertically and horizontally in rows and columns across preferably each of the absorbent material layers. The fenestrations all for full use of the absorbent capacity of the absorbent material layers and can also assist in negative pressure transmission through these layers.

In various embodiments, the dressing 14 includes an adhesive layer 150. The adhesive layer 150 may assist in securing the dressing 14 to the skin of a patient. In one embodiment, the adhesive layer 150 may also assist in creating an exterior housing or envelope with the backing layer 82, within which the inner envelope 100 resides. As shown in FIG. 3A, in one embodiment the adhesive layer 150 is connected to both the backing layer 82 and the wound contact layer 112. In particular, in such an embodiment, the backing layer 82 is adhered to an exterior portion of the adhesive layer 150 radially outwardly from an interior portion of the adhesive layer 150 to which the wound contact layer 112 is adhered. As best shown in FIG. 5A, in one embodiment the adhesive layer 150 has a perimetral shape with a central aperture 154. The aperture 154 in the adhesive layer 150 enables the skin of a user to contact, or be in fluid communication with, the wound contact layer 112 when the dressing 14 is applied to the skin of a user.

As best shown in FIG. 4, in one embodiment the backing layer first surface 83 is preferably adjacent, and in contact with, the pressure dispersing layer 104 and the adhesive layer 150, while the flexible connector 50 is disposed on the backing layer second surface 84.

A removable cover 156 may be adhered to an outer surface of the adhesive layer 150. As shown in FIGS. 3A and 5, in one embodiment the removable cover 156 may be adhered to the outer surface of the adhesive layer 150, which is located on an opposite side of the adhesive layer 150 to which the wound contact layer 112 and backing layer 82 are adhered. The removable cover 156, which may include multiple sections 156*a*, 156*b* with folded grip sections 158*a*, 158*b*, is removable from the adhesive layer 150. Thus, in a preferred embodiment the removable cover 156 protects the adhesive layer 150 when the removable cover 156 is adhered to the adhesive layer 150, but when the removable cover 156 is removed from the adhesive layer 150 for use of the dressing 14 the outer surface of the adhesive layer 150 is exposed and able to releasably secure the dressing 14 to the skin of a user.

Turning to FIGS. 7 and 8, the separable connector 44 is shown in detail along with the distal tube 40 and flexible connector 50 of the pressure tube 22. In one embodiment, the distal tube 40 includes, and preferably terminates at one end with, a distal connection portion 170. The distal connection portion 170 may include one or more distal splines 172 arranged radially around the distal connection portion 170. The distal splines 172 engage with corresponding internal splines 174 of a torque member 176 disposed around a portion of the distal tube 40. The torque member 176 assists in rotating the distal connection portion 170 to secure the distal connection portion 170 to the proximate connection portion 188.

The distal connection portion 170 also preferably includes a first mating member 180, such as threads 180, which may be helical threads. A corresponding second mating member 184, such as threads 184, may be disposed in a proximate connection portion 188, such that the distal connection portion 170 can releasably attach to the proximate connection portion 188 via the engagement of the first mating member 180 with the second mating member 184.

The combination of the internal splines 174 of the torque member 176 that are able to engage with the corresponding distal splines 172 of the distal connection portion 170 enables a user to more easily manipulate and rotate the distal connection portion 170 relative to the proximate connection portion 188 to selectively attach and detach the distal connection portion 170 to the proximate connection portion 188. FIG. 7 shows the distal connection portion 170 and the proximate connection portion 188 in an attached state, whereas FIG. 8 shows the distal connection portion 170 and the proximate connection portion 188 in a detached stated.

As shown in FIGS. 7 and 8, in one embodiment the proximate connection portion 188 is connected to, and in fluid communication with, an interface tube 194 disposed substantially between the proximate connection portion 188 and the flexible connector 50. It is to be understood that the distal tube 40, distal connection portion 170, proximate connection portion 188, interface tube 194 and flexible connector 50 are all in fluid communication with each other along the tube 22, thus enabling fluid communication between the pump 18 and the dressing 14.

In a preferred embodiment, the proximate connection portion 188 includes a one-way valve 198. The one-way valve 198 allows fluid to travel through the one-way valve 198 in a first direction while substantially or completely preventing fluid from traveling through the one-way valve 198 in a second direction. As an example, the one-way valve 198 allows fluid to flow through the proximate connection portion 188 towards the pump 18 and away from the dressing 14 while preventing fluid flow away from the pump 18 and towards the dressing 14. Such an arrangement enables a dressing 14 to continue experiencing or exhibiting negative pressure when the distal connection portion 170 and the proximate connection portion 188 are releasably detached, as shown in FIG. 8, increasing user comfort, flexibility and utility of the dressing 14 even when detached from the pump 18.

The wound exudate management system 10 preferably also includes an indicator system 200 that indicates that a fluid handling capacity of the dressing 14 has been, or shortly will be, reached and that the dressing 14 should be changed to avoid exudate leaking from the dressing 14 or entering the pump 18. The indicator system 200 may produce a signal, such as a visual, audible, vibrational, etc. signal. As an example, the indicator system 200 includes one or more of a gelling absorbent disposed within one or more of the upper absorbent indicator member 70, the backing layer 82, the pressure dispersing layer 104, the wound contact layer 112, the absorbent material layers 130*a-h* or the flexible connector 50. The gelling absorbent may include the absorbent material described above. The indicator system 200 may visually indicate that exudate has been absorbed by forming a gel. The indicator system 200 may also visually indicate that exudate has been absorbed by changing color as a result of the wound exudate entering the indicator, as a result of the wound exudate contacting some component or material within the dressing, as a result of a color-changing die activated by exudate or another fluid, or by some other means.

In some implementations, the wound exudate management system 10, and particularly the dressing 14, can be disposed in a plurality of states. For example, the dressing 14 can be in a first state where the dressing 14 is substantially free of exudate and fluids. The first state may correspond to fibers in the absorbent material of the dressing 14 having a first volume or size. Additionally, in the first state passages between the fibers have a first volume. The dressing 14 can also be in a second state where the fibers in the absorbent material of the dressing 14 have absorbed, and are partially or wholly saturated with, exudate. The first state may correspond to fibers in the absorbent material of the dressing 14 having a second volume or size. The first volume or size is relatively smaller than the second volume or size. Accordingly, the passages or openings between the fibers are relatively large. Similarly, in the second state, wherein after the fibers swell upon contact with the wound exudate, the volume or size of the passages between the fibers decreases, and the passages or openings between the fibers are relatively small or the fibers close the passages or openings. Upon continued application of negative pressure the exudate id drawn through the saturated fibers of the absorbent material to the indicator system 200.

Put another way, FIG. 1 shows a wound dressing comprising an outer cover layer, which completely overlies the other layers of the dressing, and a conduit or tube. Beneath the cover layer is an absorbent pad forming a central raised island beneath the cover layer. In one embodiment the absorbent pad comprises the plurality of absorbent material layers.

The absorbent layer is capable of absorbing exudate from the wound. The outer cover layer covers the side of the absorbent layer furthest from the wound as shown in FIGS. 3A, 4 and 5, the cover layer, also referred to as the backing layer, adapted to enable negative pressure to be applied at the wound and having a port in fluid communication with the absorbent layer. The conduit, or tubing, allows fluid communication between the port and a source of negative pressure, the conduit being connected to the outer layer by an adhesive ring. An indicator means, or upper absorbent indicator member, is provided in the port. In one embodiment the indicator means comprises a layer of gel forming fibres. Alternatively, the indicator means may also be provided still in the port, but above the cover layer. The dressing further comprises a wound contact layer adhered to the absorbent layer by a layer of heat sealable lace consisting of a polyamide lace layer. The dressing further comprises an exudate and pressure distribution layer, also referred to as a pressure dispersing layer, preferably of polyester foam which serves to spread exudate across the absorbent layer and smooth the application of negative pressure across the dressing. A further heat sealable lace layer may be provided between the distribution layer and the cover layer. The heat sealable layers assist in adhering the layers together. The absorbent layer, the wound contact layer and the indicator means comprise gel forming fibres in the form of a layer or layers carboxymethylated cellulose fabric.

In one embodiment, the absorbent layer is smaller in area than the cover layer, as shown in FIG. 5A, so that it forms an island within a frame of the cover layer. A silicone adhesive may be applied to the frame on the side of the cover layer facing the wound so as to seal the dressing to the skin surrounding the wound. Alternatively, the dressing can be secured to the wound by a perforated adhesive covering the wound facing surface of the dressing with or without a window over the adhesive pad and/or by dressing strips applied to the outer surface of the cover layer and the skin surrounding the dressing.

In use, the dressing may be secured to the skin surrounding the wound and the conduit, connected to a source of negative pressure by the connector located at the distal end of the conduit. Negative pressure is applied to the wound by the application of negative pressure through the pathway for fluid leading from the wound, through the absorbent layer, the port and to the distal end of the conduit. Exudate is absorbed by the wound contact layer and transmitted to the absorbent layer by close contact. Fenestrations which may be present in the absorbent layer, assist with the absorbance of exudate and that application of negative pressure. As exudate is absorbed by the absorbent layer it spreads beneath the distribution layer so that a greater area of the absorbent layer is accessed by the exudate and a greater capacity of the absorbent layer is used. Once the absorbent capacity of the absorbent layer has been reached, the exudate spreads towards the port and is absorbed by the indicator means which gels. The formation of the gel and possible colour change of the indicator means is visible to the user of the dressing and indicates that the dressing needs to be changed. The indicator means may also or alternatively be present in the conduit or in its lock where it can also be seen by the user and may provide additional time for dressing change before the exudate is drawn into the pump or other source of negative pressure.

While some implementations have been illustrated and described, numerous modifications come to mind without significantly departing from the spirit of the disclosure, and the scope of protection is only limited by the scope of the accompanying claims. Further, the present disclosure provides a sign base and a sign assembly having increased structural strength, improved aesthetic design, a footprint facilitating flexible sign base placement and a wheel arrangement allowing easy sign assembly transportation.

The disclosed systems and methods are well adapted to attain the ends and advantages mentioned as well as those that are inherent therein. The particular implementations disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative implementations disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of or "consist of the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of preceding a series of items, with the terms "and" or "or" to separate any of the items, modifies the list as a whole, rather than each article of the list (i.e., each item). The phrase "at least one of allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A wound exudate management system, comprising:

a pump for generating negative pressure;

a flexible connector configured to be connected to the pump, the flexible connector including a flexible connector aperture;

an upper adhesive including an upper adhesive aperture, wherein the flexible connector is adhered to the upper adhesive and the flexible connector aperture is aligned with the upper adhesive aperture;

a backing layer adhesive including a backing layer adhesive aperture;

a dressing for covering and protecting a wound, the dressing comprising:

a wound contact layer positioned between the wound and at least one layer of absorbent material, the wound contact layer capable of absorbing exudate and transmitting exudate to the absorbent material, a backing layer including a backing layer aperture wherein the upper layer adhesive is adhered to one side of backing layer and the backing layer adhesive is adhered to another side of the backing layer, wherein the upper adhesive aperture, the backing layer aperture, and the backing layer adhesive aperture are aligned to enable fluid communication to the at least one layer of absorbent material, and a pressure dispersing layer adjacent and in contact with the backing layer, the at least one layer of absorbent material positioned between the wound contact layer and the pressure dispersing layer, wherein the pressure dispersing layer serves to distribute exudate and negative pressure laterally over the dressing, a thermoplastic spun lace layer connected to the pressure dispersing layer and positioned between the pressure dispersing layer and the at least one layer of absorbent material, and a nonwoven spun lace layer connected and stitchbonded to the wound contact layer and positioned between the at least one layer of absorbent material and the wound contact layer, and an adhesive layer adjacent to and in contact with the wound contact layer, the adhesive layer including a perimetral shape having a central aperture to enable the wound to be in fluid communication with the wound contact layer;

a tube connecting the pump and the dressing, the tube having an interior lumen for placing the pump and the dressing in fluid communication via the interior lumen; and a one-way valve in-line between the pump and the dressing to maintain a negative pressure within the dressing when the pump is disconnected from the tube;

wherein the dressing comprises an envelope structure formed by joined peripheral portions of the thermoplastic spun lace layer and the nonwoven spun lace layer; and wherein the at least one layer of absorbent material is disposed within the envelope structure.

2. The wound exudate management system of claim 1, wherein the one-way valve is connected to one of the pump and the tube when the pump is disconnected from the tube.

3. The wound exudate management system of claim 1, wherein the pressure dispersing layer comprises a reticulated foam, a polyester foam, or a polyurethane foam.

4. The wound exudate management system of claim 1, wherein the wound contact layer is structurally reinforced with one or more of a structurally reinforced material, a structure, or a stitching.

5. The wound exudate management system of claim 1, wherein the at least one layer of absorbent material comprises one or more fenestrations.

6. The wound exudate management system of claim 1, further comprising an indicator positioned between the upper layer adhesive and the flexible connector and configured to provide a visual indication of the presence of exudate.

7. The wound exudate management system of claim 6, wherein the indicator is a layer of gel-forming fibers disposed as a gel in the presence of exudate.

8. The wound exudate management system of claim 7, wherein the indicator is configured to change color in response to the presence of exudate and the flexible connector is partially or entirely transparent so as to allow the indicator to be seen by the user.

9. A wound exudate management system, comprising:

a pump for generating negative pressure;

a dressing for covering and protecting a wound, the dressing comprising a plurality of layers including: a wound contact layer, a nonwoven spun lace layer connected and stitchbonded to the wound contact layer, a backing layer including a backing layer aperture, a pressure dispersing layer adjacent to and in contact with the backing layer and located in contact with the backing layer, a thermoplastic spun lace layer connected to the pressure dispersing layer, wherein the pressure dispersing layer serves to distribute exudate and negative pressure laterally across the dressing, at least one layer of absorbent material positioned between the wound contact layer and the pressure dispersing layer, and an adhesive layer adjacent to and in contact with the wound contact layer, the adhesive layer including a perimetral shape having a central aperture to enable the wound to be in fluid communication with the wound contact layer;

a flexible connector secured to the backing layer with an upper adhesive layer having an upper adhesive layer aperture, the flexible connector having an interior lumen aligned with the upper layer adhesive aperture;

a tube positioned between the flexible connector and the pump, and the tube having an interior lumen in fluid communication with the interior lumen of the flexible connector to connect the pump and the dressing; and a one-way valve in-line between the pump and the dressing to maintain a negative pressure within the dressing when the pump is disconnected from the tube.

10. The wound exudate management system of claim 9, wherein the dressing comprises an envelope structure formed by joined peripheral portions of at least two layers of the plurality of layers and the envelope structure is located between the pressure dispersing layer and the wound contact layer;

wherein the at least one layer of absorbent material is disposed within the envelope structure.

11. The wound exudate management system of claim 10, further comprising an indicator positioned between the at least one layer of absorbent material and the pump and configured to provide a visual indication of the presence of exudate.

12. The wound exudate management system of claim 11, wherein the upper adhesive layer is coupled to the flexible connector and the indicator.

13. The wound exudate management system of claim 12, wherein the upper adhesive layer aperture is positioned adjacent the indicator.

14. The wound exudate management system of claim 13, wherein the backing layer aperture is arranged substantially concentric with the upper adhesive layer aperture of the upper adhesive layer.

15. The wound exudate management system of claim 14, wherein the flexible connector is formed to include a flexible connector aperture arranged substantially concentric with the upper adhesive layer aperture of the upper adhesive layer and the backing layer aperture of the backing layer and configured to enable fluid communication between the dressing and the interior lumen of the flexible connector.

16. A wound exudate management system, comprising:

a pump for generating negative pressure;

a dressing for covering and protecting a wound, the dressing comprising a plurality of layers including: a wound contact layer including reinforced stitching made of nylon, a nonwoven spun lace layer connected and stichbonded to the wound contact layer, a backing layer having a backing layer aperture formed therein, a pressure dispersing layer adjacent and in contact with the backing layer, wherein the pressure dispersing layer serves to distribute exudate and negative pressure laterally across the dressing, a thermoplastic spun lace layer connected to the pressure dispersing layer, at least one layer of absorbent material positioned between the wound contact layer and the pressure dispersing layer, and an adhesive layer adjacent to and in contact with the wound contact layer, the adhesive layer including a perimetral shape having a central aperture to enable the wound to be in fluid communication with the wound contact layer;

a flexible connector secured to and contacting the backing layer of the dressing and having an interior lumen;

a tube positioned between the flexible connector and the pump, the tube having an interior lumen in fluid communication with the interior lumen of the flexible connector to connect the pump and the dressing;

a one-way valve in-line between the pump and the dressing to maintain a negative pressure within the dressing when the pump is disconnected from the tube; and an indicator positioned between the at least one layer of absorbent material and the pump and configured to provide a visual indication of the presence of exudate;

wherein the indicator is aligned with the aperture formed in the backing layer.

17. The wound exudate management system of claim 16, wherein the dressing comprises an envelope structure formed by joined peripheral portions of the pressure dispersing layer and the wound contact layer;

wherein pressure dispersing layer is formed of foam and the at least one layer of absorbent material is disposed within the envelope structure.

18. The wound exudate management system of claim 16, wherein at least one of the backing member and the flexible connector are transparent so as to allow the indicator to be seen by a user of the wound exudate management system.

19. The wound exudate management system of claim 1, wherein the pressure dispersing layer is formed of carboxymethylated cellulose.

20. The wound exudate management system of claim 9, wherein the pressure dispersing layer is formed of carboxymethylated cellulose.

* * * * *